United States Patent
Padi et al.

(10) Patent No.: US 8,969,558 B2
(45) Date of Patent: Mar. 3, 2015

(54) PROCESSES FOR THE PREPARATION OF SITAGLIPTIN AND PHARMACEUTICALLY ACCEPTABLE SALTS THEREOF

(71) Applicant: Dr. Reddy's Laboratories Limited, Hyderabad (IN)

(72) Inventors: Pratap Reddy Padi, Hyderabad (IN); Babu Ireni, Nizamabad (IN); Srinivas Polavarapu, Hyderabad (IN); Shailaja Padamata, Hyderabad (IN); Kavitha Nerella, Krishna District (IN); Vijaya Anand Ramasamy, Virudhunagar (IN); Ranga Reddy Vangala, Hyderabad (IN)

(73) Assignee: Dr. Reddy's Laboratories Limited, Hyderabad (IN)

( * ) Notice: Subject to any disclaimer, the term of this patent is extended or adjusted under 35 U.S.C. 154(b) by 0 days.

(21) Appl. No.: 14/097,988

(22) Filed: Dec. 5, 2013

(65) Prior Publication Data

US 2014/0128607 A1    May 8, 2014

Related U.S. Application Data

(60) Continuation of application No. 13/648,026, filed on Oct. 9, 2012, now abandoned, which is a division of application No. 12/809,200, filed as application No. PCT/US2008/087491 on Dec. 18, 2008, now Pat. No. 8,309,724.

(60) Provisional application No. 61/058,764, filed on Jun. 4, 2008, provisional application No. 61/058,975, filed on Jun. 5, 2008, provisional application No. 61/097,910, filed on Sep. 18, 2008.

(51) Int. Cl.
C07D 241/38    (2006.01)
C07D 487/04    (2006.01)

(52) U.S. Cl.
CPC ................................. C07D 487/04 (2013.01)
USPC ........................................................ 544/350

(58) Field of Classification Search
CPC .................................................... C07D 241/38
USPC .......................................................... 544/350
See application file for complete search history.

(56) References Cited

U.S. PATENT DOCUMENTS

| | | | |
|---|---|---|---|
| 6,699,871 B2 | 3/2004 | Edmondson et al. | |
| 7,265,128 B2 | 9/2007 | Ashton et al. | |
| 7,326,708 B2 | 2/2008 | Cypes et al. | |
| 7,468,459 B2 | 12/2008 | Xiao et al. | |
| 7,612,072 B2 | 11/2009 | Ferlita et al. | |
| 2005/0032804 A1 | 2/2005 | Cypes et al. | |
| 2006/0194977 A1 | 8/2006 | Xiao et al. | |
| 2006/0287528 A1 | 12/2006 | Wenslow et al. | |
| 2007/0021430 A1 | 1/2007 | Chen et al. | |
| 2008/0227786 A1 | 9/2008 | Ferlita et al. | |
| 2009/0221592 A1 | 9/2009 | Ellison et al. | |
| 2009/0247532 A1 | 10/2009 | Huang et al. | |
| 2012/0184558 A1 | 7/2012 | Winter et al. | |

FOREIGN PATENT DOCUMENTS

WO    2004/085661 A2    10/2004
WO    2004/087650 A2    10/2004

OTHER PUBLICATIONS

David J. Ager, "Novel Chiral Chemistries Japan 2007", Platinum Metals Rev., 2007, pp. 172-175, vol. 51—issue No. 4.
Berge et al., "Pharmaceutical Salts", Journal of Pharmaceutical Sciences, Jan. 1977, pp. 1-19, vol. 66—issue No. 1.
International Search Report dated Jul. 10, 2009 for corresponding International Patent Application No. PCT/US2008/087491.
Non-Final Office Action for U.S. Appl. No. 12/809,200 mailed by the USPTO on Apr. 2, 2012.
Non-Final Office Action for U.S. Appl. No. 13/648,026 mailed by the USPTO on Dec. 28, 2012.
Final Office Action for U.S. Appl. No. 13/648,026 mailed by the USPTO on Jul. 8, 2013.

*Primary Examiner* — Douglas M Willis
(74) *Attorney, Agent, or Firm* — Pergament Gilman & Cepeda LLP; Milagros A. Cepeda; Edward D. Pergament

(57) ABSTRACT

There is provided a process for preparation of sitagliptin of Formula II or a pharmaceutically acceptable salt thereof by deprotection of Formula IX.

Formula II

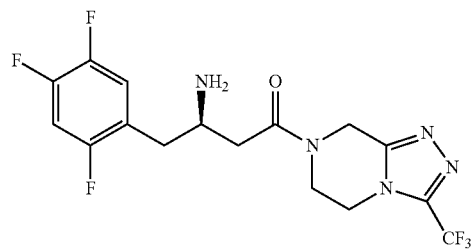

5 Claims, 33 Drawing Sheets

PROCESSES FOR THE PREPARATION OF SITAGLIPTIN AND PHARMACEUTICALLY ACCEPTABLE SALTS THEREOF

This application is a Continuation Application of U.S. patent application Ser. No. 13/648,026, filed on Oct. 9, 2012, which is a Divisional of U.S. patent application Ser. No. 12/809,200 filed Jun. 18, 2010, which claims the benefit of International Application No. PCT/US2008/087491 filed Dec. 18, 2008; Indian Application No. 3076/CHE/2007, filed Dec. 20, 2007; Indian Application No. 159/CHE/2008 filed Jan. 18, 2008; Indian Application No. 1188/CHE/2008 filed May 14, 2008; U.S. Application No. 61/058,764 filed Jun. 4, 2008; U.S. Application No. 61/058,975 filed Jun. 5, 2008 and U.S. Application No. 61/097,910 filed Sep. 18, 2008, all of which are hereby incorporate herein by reference in their entireties.

INTRODUCTION

The present application relates to sitagliptin, its salts, and its polymorphs, and processes for the preparation of sitagliptin, its salts, and its polymorphs.

Sitagliptin is (R)-7-(1-oxo-3((R)-amino)-4-(2,4,5-trifluorophenyl)-butyl)-3-(trifluoromethyl)-5,6,7,8-tetrahydro-1,2,4-triazolo[4,3-a]pyrazine represented by the structural Formula II.

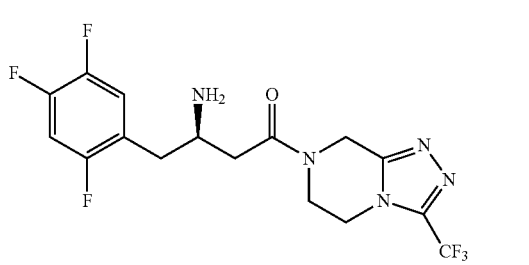

Formula II

Sitagliptin is an orally-active dipeptidyl peptidase-4 (DPP-IV) enzyme inhibitor that improves glycemic control in patients with Type 2 diabetes mellitus by slowing the inactivation of incretin hormones. Sitagliptin may be used as a monotherapy, as an adjunct to diet and exercise, or in combination with metformin or a PPARγ agonist (e.g., thiazolidinediones).

U.S. Pat. No. 6,699,871 describes a class of beta-amino-tetrahydrotriazolo[4,3-a]pyrazines that are potent inhibitors of DPP-IV and therefore useful for the treatment of Type 2 diabetes. Specifically disclosed in U.S. Pat. No. 6,699,871 is sitagliptin. Pharmaceutically acceptable salts of this compound are generically encompassed within the scope of U.S. Pat. No. 6,699,871. It also discloses a process for the preparation of sitagliptin and related compounds.

International Application Publication No. WO 2004/085661 discloses a process for the preparation of sitagliptin in which S-phenyl glycine amide is used as a chiral auxilary to form an intermediate that subsequently provides the required enantiomer sitagliptin).

International Application Publication No. WO 2004/087650 discloses another process in which N-protected 3-((R)-amino)-4-(2,4,5-trifluorophenyl)-butyric acid is synthesized enantio-selectively, condensed with a pyrazine intermediate, and deprotected to provide sitagliptin.

U.S. Pat. No. 7,326,708 discloses the dihydrogen phosphate salt of sitagliptin and processes for the preparation thereof.

International Application Publication No. WO 2004/085378 discloses a process for the preparation of sitagliptin, wherein the reduction of the sitagliptin intermediate is carried out by using rhodium metal and a chiral ferrocenyl diphosphine.

Although several processes have been reported in the prior art for the preparation of sitagliptin, they suffer from one or more drawbacks such as involving the use of hazardous regents, like platinum oxide, rhodium catalyst, etc., costly reagents, such as chloro pyrazine, dichloropyrazine, etc., and extensive protection and deprotection steps. Hence, there is an ongoing need for simple, cost effective, and industrially viable processes for the production of sitagliptin and its pharmaceutically acceptable salts.

Crystalline salts of sitagliptin are known. International Application Publication No. WO 2005/072530 describes various crystalline salts of sitagliptin, International Application Publication No. WO 2006/033848 describes amorphous form of the dihydrogen phosphate salt of sitagliptin. International Application Publication No. WO 2005/020920 discloses two crystalline anhydrous forms of the dihydrogen phosphate salt of sitagliptin namely Form I and Form III, and a crystalline desolvated anhydrate Form II. International Application Publication No. WO 2005/030127 discloses a crystalline anhydrate Form IV of the dihydrogen phosphate salt of sitagliptin. International Application Publication No. WO 2005/072530 discloses crystalline hydrochloric acid, benzenesulfonic acid, p-toluenesulfonic acid, 10-camphorsulfonic acid, and tartaric acid salts of sitagliptin. International Application Publication No. WO 2007/035198 discloses dodecylsulfate salt of sitagliptin.

There remains a need for further improvement in properties of solid sitagliptin, such as stability, purity, flowability, vapor impermeability, solubility, and bioavailability.

SUMMARY OF THE APPLICATION

The present invention includes processes for the preparation of sitagliptin, which processes comprise at least one of the steps of:

(i) reacting 7-(1,3-dioxo-4-(2,4,5-trifluorophenyl)-butyl)-3-trifluoromethyl-5,6,7,8-tetrahydro-1,2,4-triazolo[4,3-a]pyrazine with a first reagent to afford 7-(1-oxo-3-amino-4-(2,4,5-trifluorophenyl)-but-2-enyl)-3-trifluoromethyl-5,6,7,8-tetrahydro-1,2,4-triazolo[4,3-a]pyrazine;

(ii) converting the 7-(1-oxo-3-amino-4-(2,4,5-trifluorophenyl)-but-2-enyl)-3-trifluoromethyl-5,6,7,8-tetrahydro-1,2,4-triazolo[4,3-a]pyrazine with a second reagent to 7-(1-oxo-3-amino-4-(2,4,5-trifluorophenyl)-butyl)-3-(trifluoromethyl)-5,6,7,8-tetrahydro-1,2,4-triazolo[4,3-a]pyrazine;

(iii) treating the 7-(1-oxo-3-amino-4-(2,4,5-trifluorophenyl)-butyl)-3-(trifluoromethyl)-5,6,7,8-tetrahydro-1,2,4-triazolo[4,3-a]pyrazine with a third reagent to afford a diastereomeric salt of 7-(1-oxo-3((R)-amino)-4-(2,4,5-trifluorophenyl)-butyl)-3-(trifluoromethyl)-5,6,7,8-tetrahydro-1,2,4-triazolo[4,3-a]pyrazine;

(iv) isolating the diastereomeric salt;

(v) treating the diastereomeric salt with an acid or a base to afford sitagliptin freebase; and (vi) optionally treating the sitagliptin freebase with an acid to afford an acid addition salt of sitagliptin.

The present invention includes processes for the preparation of sitagliptin, which processes comprise at least one of the steps of:

(i) reacting 7-(1,3-dioxo-4-(2,4,5-trifluorophenyl)-butyl)-3-trifluoromethyl-5,6,7,8-tetrahydro-1,2,4-triazolo[4,3-a]pyrazine with a chiral reagent to produce the compound of the Formula VIII, wherein R is an $C_1$-$C_4$ alkyl;

(ii) converting the compound of Formula VIII to the compound of Formula IX, wherein wherein R is as defined above;

(iii) converting the compound of Formula VIII using an acid or base or a catalyst to afford sitagliptin freebase (iv) optionally treating the sitagliptin freebase with an acid to afford an acid addition salt of sitagliptin.

The present invention includes anhydrous crystalline sitagliptin dihydrogen phosphate of Formula I' (also referred to hereinafter as Form A).

Form A may be characterized by differential scanning calorimetry (DSC) thermogram with onset at about 201° C. and endotherm peak at about 205.5° C.

Form A may also be characterized by its X-ray diffraction pattern with characteristic peaks at diffraction angles 2-theta of about 4.58, 9.23, 12.24, 13.88, 18.23, 23.63, 24.24, and 26.68±0.2 degrees.

Form A may also be characterized by X-ray diffraction pattern substantially as shown in FIG. 1.

Also, Form A may be characterized by thermo gravimetric analysis (TGA) curve corresponding to a weight loss of about 0.038% (0.01082 mg) up to a temperature of about 100° C. (as shown in FIG. 3).

The present invention includes processes for the preparation of Form A, which processes comprise the step of treating sitagliptin freebase with phosphoric acid in aqueous isopropanol having a water content of less than about 6%.

In addition to Form A, the present invention includes the sulfuric acid, hydrobromic acid, methanesulfonic acid, acetic acid, benzoic acid, oxalic acid, succinic acid, mandelic acid, fumaric acid, and lactic acid salts of sitagliptin.

The present invention includes processes for the preparation of salts of sitagliptin, which processes comprise at least one of the steps of:

(a) providing a solution of a salt of sitagliptin in a solvent;
(b) isolating the salt of sitagliptin from the solution of Step (a); and
(c) recovering the crystalline salt of sitagliptin and optionally drying it.

There present invention includes pharmaceutical compositions comprising sitagliptin according to the present invention together with at least one pharmaceutically acceptable excipient.

DETAILED DESCRIPTION

Figure 1:
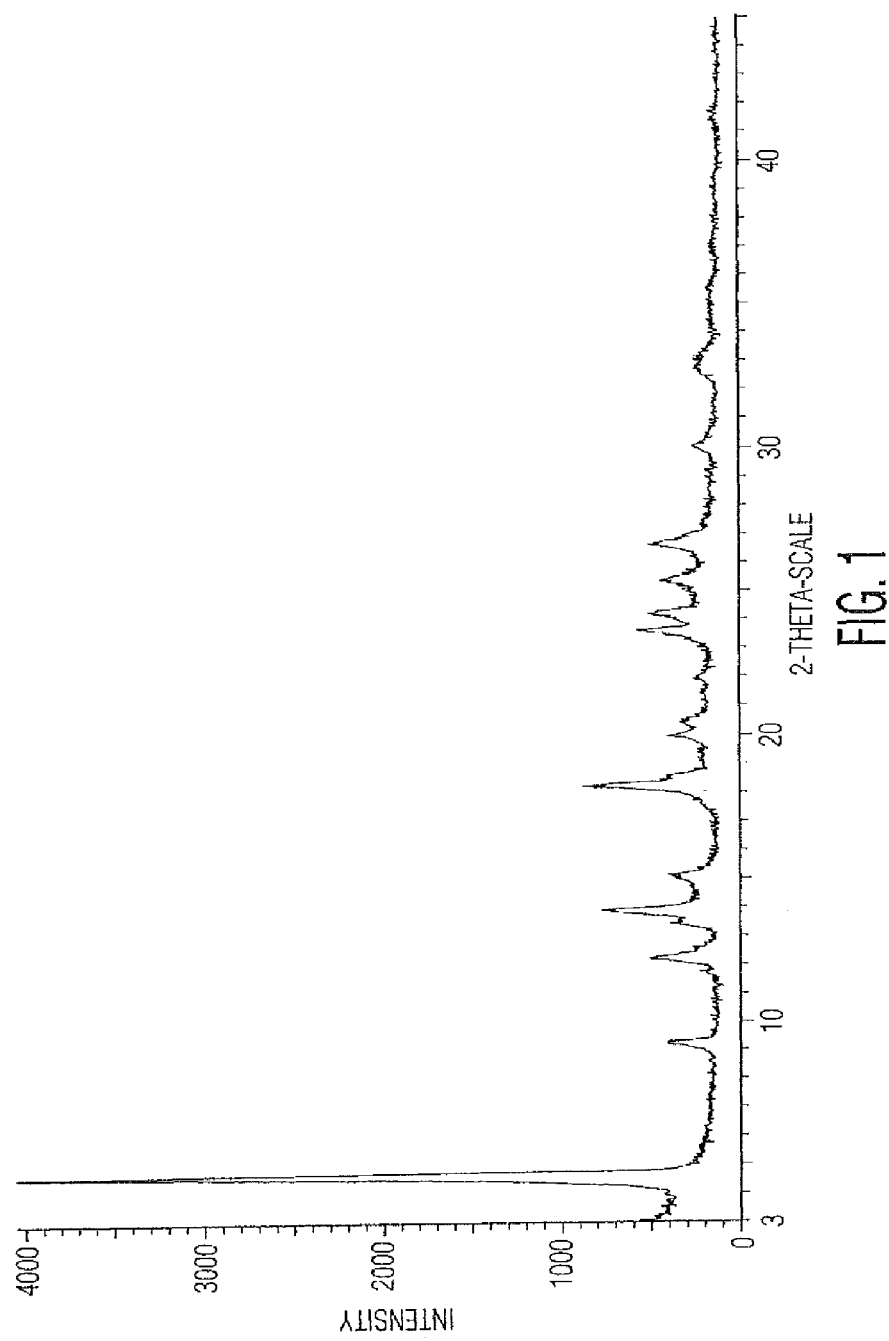
FIG. 1 is an illustration of X-ray powder diffraction (XRPD) pattern of crystalline anhydrate Form A of the dihydrogen phosphate salt of sitagliptin.
Figure 2:
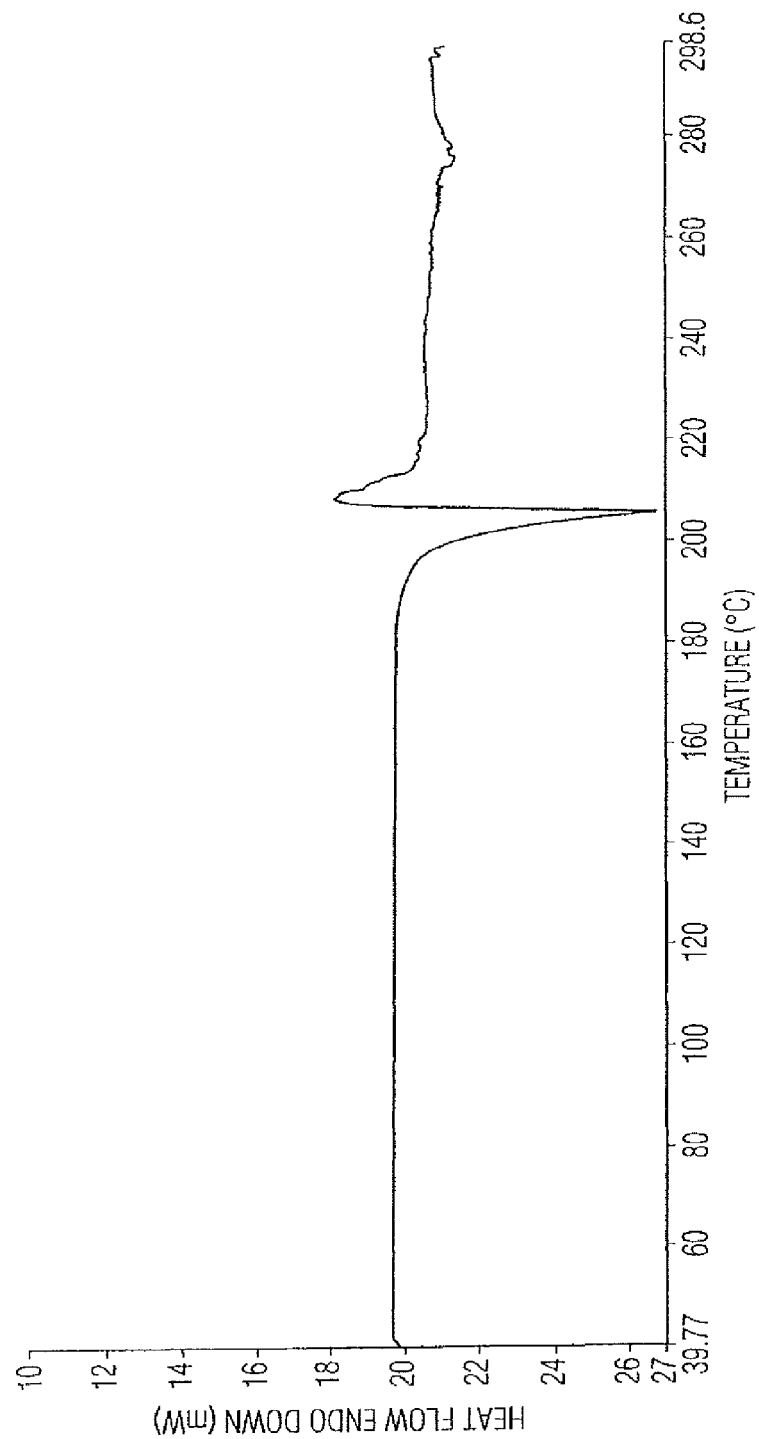
FIG. 2 is an illustration of differential scanning calorimetry ("DSC") curve of crystalline anhydrate Form A of the dihydrogen phosphate salt of sitagliptin.

All percentages and ratios used herein are by weight of the total composition and all measurements made are at 25° C. and normal pressure unless otherwise designated. All temperatures are in Degrees Celsius unless specified otherwise.

The present invention can comprise (open ended) of the components of the present invention as well as other ingredients or elements described herein.

As used herein, "comprising" means the elements recited, or their equivalent in structure or function, plus any other element or elements which are not recited. The terms "having" and "including" are also to be construed as open ended unless the context suggests otherwise.

All ranges recited herein include the endpoints, including those that recite a range "between" two values.

Terms such as "about," "generally," "substantially," and the like are to be construed as modifying a term or value such that it is not an absolute, but does not read on the prior art. Such terms will be defined by the circumstances and the terms that they modify as those terms are understood by those of skill in the art. This includes, at very least, the degree of expected experimental error, technique error and instrument error for a given technique used to measure a value.

This document may refer to a material, such as in this instance, salts of sitagliptin, and its crystalline forms, solvates, or optical isomers by reference to patterns, spectra, or other graphical data, "substantially" as shown in a Figure, or by one or more data points. By "substantially" used in such a context, it will be appreciated that patterns, spectra, and other graphical data can be shifted in their positions, relative intensities, and/or values due to a number of factors known to those of skill in the art. For example, in the crystallographic and powder X-ray diffraction arts, such shifts in peak positions or the relative intensities of one or more peaks can occur because of, without limitation: the equipment used, the sample preparation protocol, preferred packing and orientations, the radiation source, operator error, method and length of data collection, and the like. However, those of ordinary skill in the art should be able to compare the figures herein with a pattern generated of an unknown form of, in this case, salts of sitagliptin, and confirm its identity as one of the forms disclosed and claimed herein. The same holds true for other techniques which may be reported herein.

In addition, where a reference is made to a figure, it is permissible to, and this document includes and contemplates, the selection of any number of data points illustrated in the figure that uniquely define that crystalline form, salt, or optical isomer.

When a molecule or other material is identified herein as "pure", it generally means, unless specified otherwise, that the material is 99% pure or more, as determined by methods conventional in art such as high performance liquid chromatography (HPLC) or optical methods. In general, this refers to purity with regard to unwanted residual solvents, reaction byproducts, impurities and unreacted starting materials. In the case of stereoisomers, "pure" also means 99% of one enantiomer or diastereomer, as appropriate. "Substantially pure" refers to the same as "pure except that the lower limit is about 98% pure or more and likewise, "essentially pure" means the same as "pure" except that the lower limit is about 95% pure.

As used herein, the terms "salt(s) of sitagliptin," "sitagliptin salt(s)" and other similar phrases encompass crystalline and amorphous forms, solvates, hydrates, stereoisomers, both individual and in mixtures thereof, racemates, enantiomers, and the like The present invention includes processes for the preparation of sitagliptin, which processes comprise at least one of the steps of:

(i) reacting 7-(1,3-dioxo-4-(2,4,5-trifluorophenyl)-butyl)-3-trifluoromethyl-5,6,7,8-tetrahydro-1,2,4-triazolo[4,3-a]pyrazine of Formula VI Formula VI

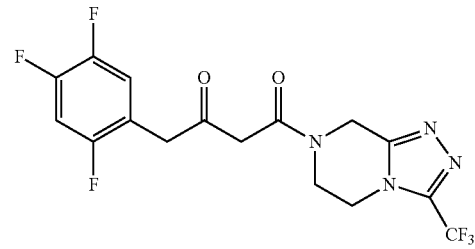

with a reagent, optionally in the presence of a solvent, to afford 7-(1-oxo-3-amino-4-(2,4,5-trifluorophenyl)-but-2-enyl)-3-trifluoromethyl-5,6,7,8-tetrahydro-1,2,4-triazolo[4,3-a]pyrazine of Formula V;

Formula V

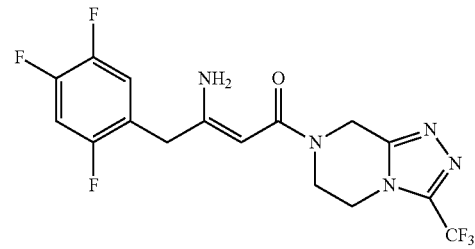

(ii) converting the compound of Formula V to 7-(1-oxo-3-amino-4-(2,4,5-trifluorophenyl)-butyl)-3-(trifluoromethyl)-5,6,7,8-tetrahydro-1,2,4-triazolo[4,3-a]pyrazine of Formula IV;

Formula IV

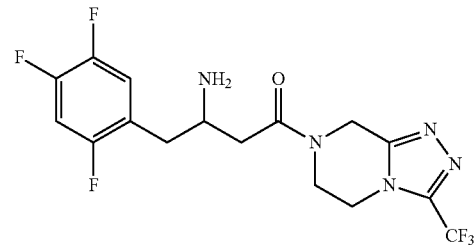

(iii) treating the compound of Formula IV with a reagent to afford a diasteromeric salt of sitagliptin of Formula III;

Formula III

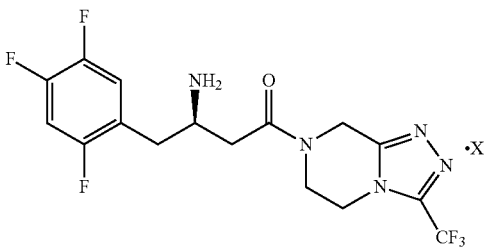

wherein X is the reagent used for the preparation of said diasteromeric salt;

(iv) isolating the diasteromeric salt of sitagliptin;
(v) treating the diasteromeric salt of sitagliptin with an acid or a base to afford sitagliptin freebase of Formula II;

Formula II

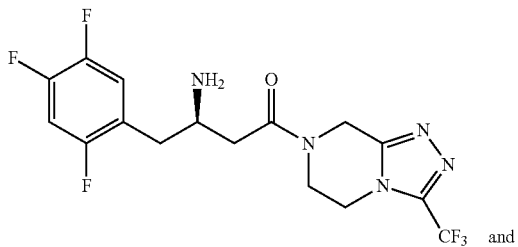

and (vi) optionally treating the sitagliptin freebase with an acid to afford an acid addition salt of sitagliptin of Formula I Formula I

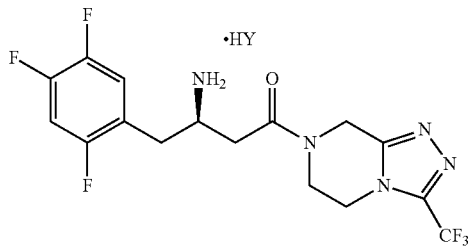

wherein Y is an acid residue.

Step (i) involves reacting the compound of Formula VI with a reagent, optionally in a solvent, to afford the compound of the formula (V)

Suitable reagents include and are not limited to ammonia sources, such as, for example, ammonium chloride, ammonium bromide, ammonium iodide, ammonium carbonate, ammonium formate, ammonium acetate, formamide, ammonium formate in combination with methanolic ammonia or ethanolic ammonia, ammonium formate in combination with isopropanol ammonia, ammonium formate in combination with aqueous ammonia, ammonium formate in combination with formic acid, formamide in combination with formic acid, formamide in combination with formic acid and isopropanol ammonia, formamide in combination with formic acid and methanolic ammonia, formamide in combination with formic acid and aqueous ammonia, or a mixture thereof. For example, the ammonia source may be ammonium acetate in combination with aqueous ammonia.

Suitable solvents that may be used include and are not limited to, alcohols, such as, for example methanol, ethanol, isopropanol, n-butanol, and the like; nitriles like acetonitrile, propionitrile, and the like; ketones, such as, for example, acetone, methyl isobutyl ketone, methyl ethyl ketone, n-butanone, and the like; halogenated solvents, such as, for example, dichloromethane, ethylene dichloride, chloroform, and the like; esters, such as, for example ethyl acetate, n-propyl acetate, isopropyl acetate, and the like; hydrocarbon solvents, such as, for example, toluene, xylene, n-hexane, n-heptane, cyclohexane, and the like; ethers, such as, for example, 1,4-dioxane, tetrahydrofuran, and the like; aprotic polar solvents, such as, for example, N,N-dimethylformamide (DMF), dimethylsulfoxide (DMSO), dimethylacetamide (DMA); water; or mixtures thereof.

A suitable temperature for the reaction of Step (i) may be less than about 150° C., or less than about 120° C., or less than about 80° C., or less than about 60° C., or any other suitable temperatures.

Step (ii) involves conversion of the compound of the Formula V to a compound of Formula IV.

Suitable reagents that may be used for the conversion include and are not limited to sodium borohydride, lithium aluminium hydride, vitride, sodium cyano borohydride, palladium-carbon, RANEY nickel, and platinum oxide, or any other suitable reagent. For example, the reagent may be sodium cyano borohydride.

Suitable solvents that may be used include and are not limited to, alcohols, such as, for example methanol, ethanol, isopropanol, n-butanol, and the like; nitriles like acetonitrile, propionitrile, and the like; ketones, such as, for example, acetone, methyl isobutyl ketone, methyl ethyl ketone, n-butanone, and the like; halogenated solvents, such as, for example, dichloromethane, ethylene dichloride, chloroform, and the like; esters, such as, for example ethyl acetate, n-propyl acetate, isopropyl acetate, and the like; hydrocarbon solvents, such as, for example, toluene, xylene, n-hexane, n-heptane, cyclohexane, and the like; ethers, such as, for example, 1,4-dioxane, tetrahydrofuran, and the like; aprotic polar solvents, such as, for example, N,N-dimethylformamide (DMF), dimethylsulfoxide (DMSO), dimethylacetamide (DMA); water; or mixtures thereof.

A suitable temperature for the reaction of Step (ii) may be less than about 250° C., or less than about 200° C., or less than about 150° C., or less than about 100° C., or less than about 80° C., or less than about 60° C., or any other suitable temperature.

The reaction may be carried out for any desired time period ranging from about 30 minutes to about 10 hours or longer.

Step (iii) involves treating the compound of Formula IV with a reagent to afford a diasteromeric salt of sitagliptin of Formula III Suitable reagents that may be used include and are not limited to: S-(+)-mandelic acid, R-(−)-mandelic acid, (1S)-(+)-camphor-10-sulfonic acid, (1R)-(−)-camphor-10-sulfonic acid, L-malic acid, D-malic acid, L-maleic acid, D-maleic acid, (−)-naproxen, (+)-naproxen, (−)-ibuprofen, (+)-ibuprofen, (1R)-(+)-3-bromocamphor-10-sulfonic acid, (1S)-(−)-3-bromocamphor-10-sulfonic acid, L-(+)-tartaric acid, D-(−)-tartaric acid, (+)-dibenzoyl-D-tartaric acid, (−)-dibenzoyl-L-tartaric acid, (+)-dipara-tolyl-D-tartaric acid, (−)-dipara-tolyl-L-tartaric acid, L-(−)-pyroglutamic acid, L-(+)-pyroglutamic acid, (−)-lactic acid, L(+)-lactic acid, L-lysine, D-lysine, and mixtures of thereof. For example, the reagent may be (−)-di-para-tolyl-L-tartaric acid Suitable solvents that may be used include and are not limited to, alcohols, such as, for example methanol, ethanol, isopropanol, n-butanol, and the like; nitriles like acetonitrile, propionitrile, and the like; ketones, such as, for example, acetone, methyl isobutyl ketone, methyl ethyl ketone, n-butanone, and the like; halogenated solvents, such as, for example, dichloromethane, ethylene dichloride, chloroform, and the like; esters, such as, for example ethyl acetate, n-propyl acetate, isopropyl acetate, and the like; hydrocarbon solvents, such as, for example, toluene, xylene, n-hexane, n-heptane, cyclohexane, and the like; ethers, such as, for example, 1,4-dioxane, tetrahydrofuran, and the like; aprotic polar solvents, such as, for example, N,N-dimethylformamide (DMF), dimethylsulfoxide (DMSO), dimethylacetamide (DMA); water; or mixtures thereof.

A suitable temperature for the reaction of Step (iii) may be less than about 150° C., or less than about 120° C., or less than about 80° C., or less than about 60° C., or any other suitable temperatures.

The reaction may be carried out for any desired time periods ranging from about 30 minutes to about 30 hours or longer.

Step (iv) involves isolating the diasteromeric salt of sitagliptin of Formula III The diastereomeric salt formed in Step (iii) may be recovered by conventional methods including decantation, centrifugation, gravity filtration, suction filtration, or other techniques known in the art for the recovery of solids. The recovered solid may be further dried. Drying may be suitably carried out using a tray dryer, vacuum oven, air oven, fluidized bed drier, spin flash dryer, flash dryer, and the like at atmospheric pressure or under reduced pressure. Drying may be carried out at a temperature of less than about 150° C., or less than 120° C., or less than 100° C., or less than about 60° C., or less than about 40° C., or any other suitable temperature, at atmospheric pressure or under reduced pressure, and in the presence or absence of an inert atmosphere such as nitrogen, argon, neon, or helium. The drying may be carried out for any desired time period to achieve the desired quality of the product, such as, for example, about 1 to about 15 hours or longer.

The diasteromeric salt of Formula III may be purified by processes known in the art. For example, the diasteromeric salt of Formula III may be purified by precipitation or making a slurry in a suitable solvent. Precipitation may be achieved by methods such as crystallization, adding an anti-solvent to a concentrated solution of the said diastereomeric salt, or any other suitable method known in the art.

Step (v) involves treating the diasteromeric salt of Formula III with an acid or a base to afford sitagliptin freebase of Formula II.

Suitable bases that may be used for treating the diasteromeric salt of Formula II include and are not limited to: inorganic bases, such as, for example, sodium hydroxide, potassium hydroxide, sodium methoxide, potassium teritarybutoxide, sodium teritarybutoxide, sodium carbonate, potassium carbonate, sodium bicarbonate, potassium bicarbonate, and the like, either alone or as their aqueous solutions; organic bases, such as, for example, triethylamine, pyridine, N-methyl Morpholine, diisopropyl amine, diisopropyl ethylamine, and the like; resins, such as, for example, ion exchange resins; and mixtures thereof.

Suitable acids that may be used for treating the diasteromeric salt of Formula II include and are not limited to: inorganic acids, such as, for example, hydrochloric acid, nitric acid, sulphuric acid, phosphoric acid, and the like; organic acids, such as, for example, acetic acid, propionic acid, butyric acid, and the like; and mixtures thereof.

Suitable solvents that may be used in Step (v) include and are not limited to: alcohols, such as, for example, ketones, such as, for example, methyl isobutyl ketone, methyl ethyl ketone, n-butanone, and the like; halogenated solvents, such as, for example, dichloromethane, ethylene dichloride, chloroform, and the like; esters, such as, for example, ethyl acetate, n-propyl acetate, isopropyl acetate, and the like; hydrocarbon solvents, such as, for example, toluene, xylene, cyclohexane, and the like; ethers, such as, for example, 1,4-dioxane, tetrahydrofuran, and the like; and mixtures thereof.

A suitable temperature for Step (v) may be less than about 150° C., or less than about 120° C., or less than about 80° C., or less than about 60° C., or any other suitable temperatures.

A suitable time for the reaction of Step (v) may be from about 30 minutes to about 20 hours or longer to achieve the desired yield and quality.

Step (vi) involves optionally treating sitagliptin freebase with an acid to afford an acid addition salt of sitagliptin of Formula I Suitable acids for Step (vi) include and are not limited to phosphoric acid, hydrochloric acid, oxalic acid, hydrobromic acid, acetic acid, formic acid, citric acid, and the like.

Conversion of the acid addition salt of sitagliptin of Formula I into sitagliptin freebase is also contemplated.

For example, sitagliptin free base may be treated with phosphoric acid to afford sitagliptin phosphate of Formula (I'). For the reaction, the molar equivalents of phosphoric acid that may be used may range from about 0.5 to about 2.0 molar equivalents with respect to sitagliptin free base.

The acid addition salt of sitagliptin of Formula I obtained in Step (vi) may be dried. Drying may be carried out in a tray dryer, vacuum oven, air oven, fluidized bed drier, spin flash dryer, flash dryer and the like, at atmospheric pressure or under reduced pressure.

The drying may be carried out at temperatures of less than about 100° C., or less than about 90° C., or less than about 60° C., or less than about 50° C., or any other suitable temperature at atmospheric pressure or under reduced pressure. The drying may be carried out for any desired time ranging from about 1 to 20 hours or longer.

Optionally, the salt of sitagliptin may be purified by processes known in the art. For example, the salt of sitagliptin may be purified by precipitation or making a slurry in a suitable solvent. The precipitation may be achieved by crystallization, by adding an anti-solvent, or any other suitable method known in the art.

The present invention includes stereoselective processes for the preparation of sitagliptin, which processes comprise at least one of the steps of:

(i) reacting 7-(1,3-dioxo-4-(2,4,5-trifluorophenyl)-butyl)-3-trifluoromethyl-5,6,7,8-tetrahydro-1,2,4-triazolo[4,3-a]pyrazine of Formula VI:

Formula VI

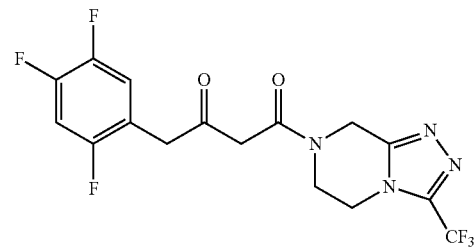

with a chiral reagent of Formula VII:

Formula VII

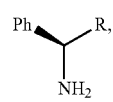

wherein R is $C_1$-$C_4$ alkyl, to produce the compound of the Formula VIII;

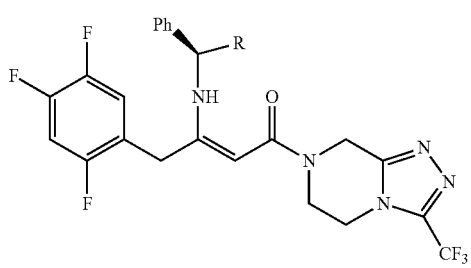

Formula VIII (ii) converting the compound of Formula VIII to the compound of Formula IX

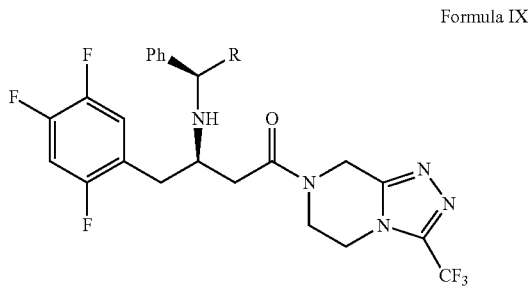

Formula IX (iii) converting the compound of Formula VIII using an acid or base or a catalyst to afford sitagliptin freebase of Formula II; and

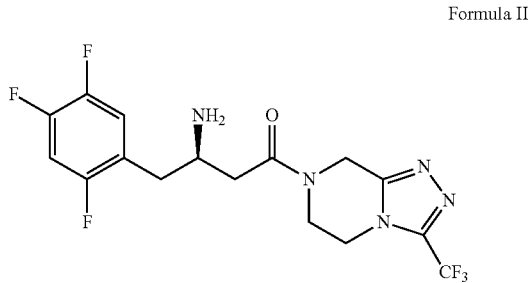 [SMILES: N[C@@H](CC(=O)N1CCn2c(nnc2C(F)(F)F)C1)Cc1cc(F)c(F)cc1F]

Formula II (iv) optionally treating the sitagliptin freebase with an acid to afford an acid addition salt of sitagliptin of Formula I

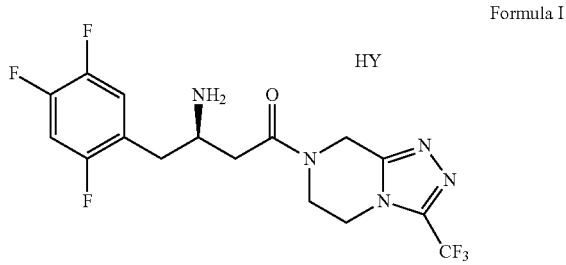

Formula I wherein Y is an acid residue.

Step (i) involves reacting the compound of the formula VI with a chiral compound of Formula VII to produce a chiral enamine of Formula VIII.

For example, the chiral reagent may be (R)-1-phenylethylamine.

For the reaction of Step (i), the molar equivalents of the chiral compound of Formula VII may range from about 1.0 to about 2.0 molar equivalents with respect to the compound of Formula VI.

The reaction of Step (i) may be conducted in a solvent. Solvents that may be used include and not limited to: alcohols, such as, for example, methanol, ethanol, isopropanol, and n-butanol; organic acids, such as, for example, acetic acid and propionic acid; ketones, such as, for example, acetone, methyl isobutyl ketone, methyl ethyl ketone, and n-butanone; halogenated solvents, such as, for example, dichloromethane, ethylene dichloride, and chloroform; esters, such as, for example, ethyl acetate, n-propyl acetate, and isopropyl acetate; hydrocarbon solvents, such as, for example, toluene, xylene, n-hexane, n-heptane, and cyclohexane; ethers, such as, for example, 1,4-dioxane, and tetrahydrofuran; organic acids, such as, for example, acetic acid, propionic acid, and the like; and mixtures thereof.

A suitable temperature for the reaction of Step (i) may be less than about 150° C., or less than about 120° C., or less than about 80° C., or less than about 60° C., or any other suitable temperatures.

A suitable time for the reaction of Step (i) may be from about 30 minutes to about 10 hours or longer.

Step (ii) involves converting the compound of Formula VIII to a compound of Formula IX.

The conversion may be achieved by methods including and not limited to reduction. A reduction may be carried out in the presence of a catalyst, such as, for example, platinum oxide ($PtO_2$). The molar equivalents of reduction catalyst may range from about 0.05 to about 1.0 molar equivalent with respect to the compound of Formula VIII.

Solvents that may be used as in Step (ii) include and are not limited to alcohols, such as, for example, methanol, ethanol, isopropanol, and n-butanol; organic acids, such as, for example, acetic acid and propionic acid; ketones, such as, for example, acetone, methyl isobutyl ketone, methyl ethyl ketone, and n-butanone; halogenated solvents, such as, for example, dichloromethane, ethylene dichloride, and chloroform; esters, such as, for example, ethyl acetate, n-propyl acetate, and isopropyl acetate; hydrocarbon solvents, such as, for example, toluene, xylene, n-hexane, n-heptane, and cyclohexane; ethers, such as, for example, 1,4-dioxane and tetrahydrofuran; aprotic polar solvents, such as, for example, N,N-dimethylformamide (DMF), dimethylsulfoxide (DMSO), and dimethylacetamide (DMA); or mixtures thereof.

A suitable temperature for the reaction of Step (ii) may be less than about 200° C., or less than about 150° C., or less than about 100° C., or less than about 60° C., or any other suitable temperatures.

A suitable time for the reaction of Step (ii) may be from about 30 minutes to about 10 hours or longer.

Step (iii) involves converting the compound of Formula IX using an acid or base or a catalyst to afford sitagliptin freebase of Formula II.

The conversion of Step (iii) may be achieved by techniques known in the art. For example, the conversion of Step (iii) may be achieved by hydrogenation in the presence of a catalyst, such as, for example, palladium on carbon, nickel on carbon, and palladium hydroxide on carbon.

Solvents that may be used as in Step (iii) include and are not limited to alcohols, such as, for example, methanol, ethanol, isopropanol, and n-butanol; organic acids, such as, for example, acetic acid and propionic acid; ketones, such as, for example, acetone, methyl isobutyl ketone, methyl ethyl ketone, and n-butanone; halogenated solvents, such as, for example, dichloromethane, ethylene dichloride, and chloroform; esters, such as, for example, ethyl acetate, n-propyl acetate, and isopropyl acetate; hydrocarbon solvents, such as, for example, toluene, xylene, n-hexane, n-heptane, and cyclohexane; ethers, such as, for example, 1,4-dioxane and tetrahydrofuran; aprotic polar solvents, such as, for example, N,N-dimethylformamide (DMF), dimethylsulfoxide (DMSO), and dimethylacetamide (DMA); or mixtures thereof.

A suitable temperature for the reaction of Step (ii) may be less than about 200° C., or less than about 150° C., or less than about 100° C., or less than about 60° C., or any other suitable temperatures.

A suitable time for the reaction of Step (ii) may be from about 30 minutes to about 10 hours or longer.

Step (iv) involves optionally treating the sitagliptin freebase of Formula II with an acid to afford an acid addition salt of sitagliptin of Formula I.

Suitable acids for Step (iv) include and are not limited to phosphoric acid, hydrochloric acid, oxalic acid, hydrobromic acid, acetic acid, formic acid, citric acid, and the like.

Conversion of the acid addition salt of sitagliptin of Formula I into sitagliptin freebase is also contemplated.

For example, sitagliptin free base may be treated with phosphoric acid to afford sitagliptin phosphate of Formula I'. For the reaction, the molar equivalents of phosphoric acid that may be used may range from about 0.5 to about 2.0 molar equivalents with respect to sitagliptin free base.

The acid addition salt of sitagliptin of Formula I obtained in Step (vi) may be dried. Drying may be carried out in a tray dryer, vacuum oven, air oven, fluidized bed drier, spin flash dryer, flash dryer and the like, at atmospheric pressure or under reduced pressure. The drying may be carried out at temperatures of less than about 100° C., or less than about 90° C., or less than about 60° C., or less than about 50° C., or any other suitable temperature at atmospheric pressure or under reduced pressure. The drying may be carried out for any desired time ranging from about 1 to 20 hours or longer.

Optionally, the salt of sitagliptin may be purified by processes known in the art. For example, the salt of sitagliptin may be purified by precipitation or making a slurry in a suitable solvent. The precipitation may be achieved by crystallization, by adding an anti-solvent, or any other suitable method known in the art.

Sitagliptin freebase and the pharmaceutically acceptable salts thereof prepared in accordance with the processes described in the present application are substantially free of process or structure related impurities, meaning the sitagliptin freebase or pharmaceutically acceptable salt thereof comprises less than about 0.5%, or less than about 0.3%, or less than about 0.2%, or less than about 0.1%, or less than about 0.05% by weight of its corresponding process or structural related impurities.

The present invention includes processes for the preparation of a compound of Formula VI, which processes comprise at least one of the steps of:

(i) reacting 2,4,5-trifluorophenylacetic acid of Formula XIII with 2,2-dimethyl-1,3-dioxane-4,6-dione (meldrums acid) of Formula XII

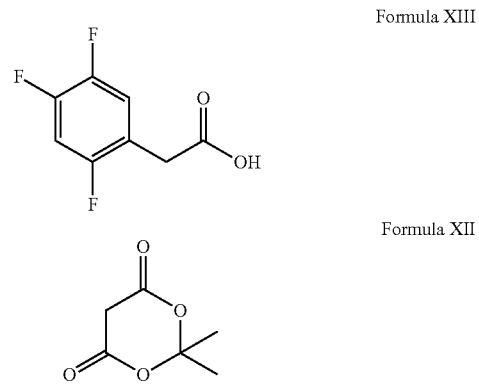

in the presence of 1,1-carbonyl diimidazole to afford 5-(1-hydroxy-2-(2,4,5-trifluorophenyl)-ethylidene)-2,2-dimethyl-1,3-dioxane-4,6-dione of Formula XI;

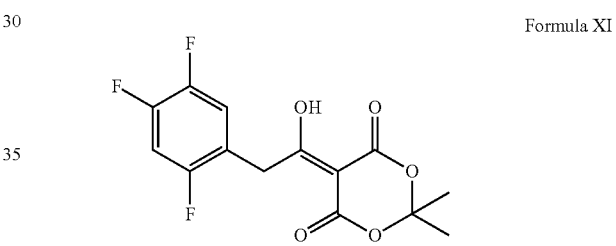

and (ii) reacting the compound of Formula XI with 3-trifluoromethyl-5,6,7,8-tetrahydro-1,2,4-triazolo[4,3-a]pyrazine hydrochloride of Formula X

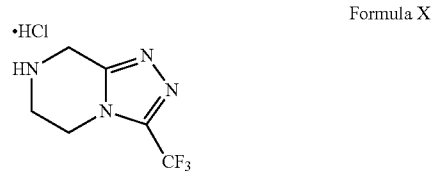 [SMILES: Cl ; FC(F)(F)c1nnc2n1CCNC2]

in the presence of diisopropylethylamine to afford compound of Formula VI.

Step (i) involves condensation of 2,4,5-trifluorophenylacetic acid of Formula XIII with 2,2-dimethyl-1,3-dioxane-4,6-dione (meldrums acid) of Formula XII.

The molar equivalents of meldrums acid that may be used in Step (i) may be less than about 2.0, or less than about 3.0, or less than about 5.0 molar equivalents with respect to the compound of Formula XIII.

Bases that may be used in Step (i) include and are not limited to: organic bases, such as, for example, triethyl amine, diisopropyl ethylamine, pyridine, imidazole, N-methyl morpholine, sodium methoxide, diisopropyl amine, 1,1-carbonyl diimidazole, and the like, inorganic bases, such as, for example, sodium carbonate, potassium carbonate, sodium bicarbonate, and potassium bicarbonate; or mixtures thereof.

Organic solvents that may be used in Step (i) include and are not limited to: alcohols, such as, for example, methanol, ethanol, isopropanol, n-butanol, and the like; organic acids, such as, for example, acetic acid, propionic acid, and the like; ketones, such as, for example, acetone, methyl isobutyl ketone, methyl ethyl ketone, n-butanone, and the like; halogenated solvents, such as, for example, dichloromethane, ethylene dichloride, chloroform, and the like; esters, such as, for example, ethyl acetate, n-propyl acetate, isopropyl acetate, and the like; hydrocarbon solvents, such as, for example, toluene, xylene, n-hexane, n-heptane, cyclohexane, and the like; ethers, such as, for example, 1,4-dioxane, tetrahydrofuran, and the like; aprotic polar solvents, such as, for example, N,N-dimethylformamide (DMF), dimethylsulfoxide (DMSO), and dimethylacetamide (DMA); water; and mixtures thereof.

A suitable temperature for the reaction of Step (ii) may be less than about 120° C., or less than about 100° C., or less than about 60° C., or any other suitable temperatures.

A suitable time for the reaction of Step (ii) may be from about 30 minutes to about 10 hours or longer.

Step (ii) involves preparation of the compound of Formula VI by reacting compound of Formula XI with 3-trifluoromethyl-5,6,7,8-tetrahydro-1,2,4-triazole[4,3-a]pyrazine hydrochloride of Formula X in the presence of diisopropylethylamine in an organic solvent to afford compound of Formula VI.

3-trifluoromethyl-5,6,7,8-tetrahydro-1,2,4-triazole[4,3-a] pyrazine hydrochloride of Formula X may be prepared, e.g., by the process of Reference Example 1 herein or as disclosed in U.S. Pat. No. 7,326,708, which patent is incorporated herein by reference in its entirety.

The molar equivalents of 3-trifluoromethyl-5,6,7,8-tetrahydro-1,2,4-triazole[4,3-a]pyrazine hydrochloride of Formula X may be less than about 3.0, or less than about 2.0, or less than about 1.0 molar equivalents with respect to the compound of Formula XI.

The molar equivalents of diisopropylethylamine may be less than about 3.0, or less than about 2.0, or less than about 1.0 molar equivalents with respect to the compound of Formula XI.

Solvents that may be used as in Step (iii) include and are not limited to alcohols, such as, for example, methanol, ethanol, isopropanol, and n-butanol; organic acids, such as, for example, acetic acid and propionic acid; ketones, such as, for example, acetone, methyl isobutyl ketone, methyl ethyl ketone, and n-butanone; halogenated solvents, such as, for example, dichloromethane, ethylene dichloride, and chloroform; esters, such as, for example, ethyl acetate, n-propyl acetate, and isopropyl acetate; hydrocarbon solvents, such as, for example, toluene, xylene, n-hexane, n-heptane, and cyclohexane; ethers, such as, for example, 1,4-dioxane and tetrahydrofuran; aprotic polar solvents, such as, for example, N,N-dimethylformamide (DMF), dimethylsulfoxide (DMSO), and dimethylacetamide (DMA); or mixtures thereof.

A suitable temperature for the reaction of Step (ii) may be less than about 120° C., or less than about 80° C., or less than about 60° C., or any other suitable temperatures.

A suitable time for the reaction of Step (ii) may be from about 30 minutes to about 10 hours or longer.

The processes of the present invention may be used to make anhydrous crystalline sitagliptin dihydrogen phosphate of Formula I' (also referred to hereinafter as Form A).

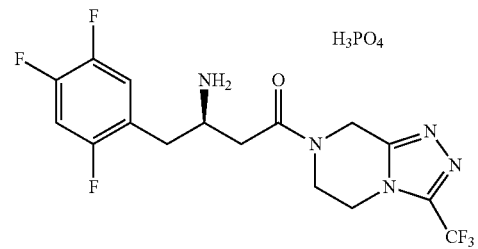

Formula I'

Form A may be characterized by differential scanning calorimetry (DSC) thermogram with onset at about 201° C. and endotherm peak at about 205.5° C.

Form A may also be characterized by its XPRD characteristic peaks at diffraction angles 2-theta of about 4.58, 9.23, 12.24, 13.88, 18.23, 23.63, 24.24, and 26.68±0.2 degrees.

Form A may also be characterized by the X-ray diffraction pattern substantially as shown in FIG. 1.

Figure 3:
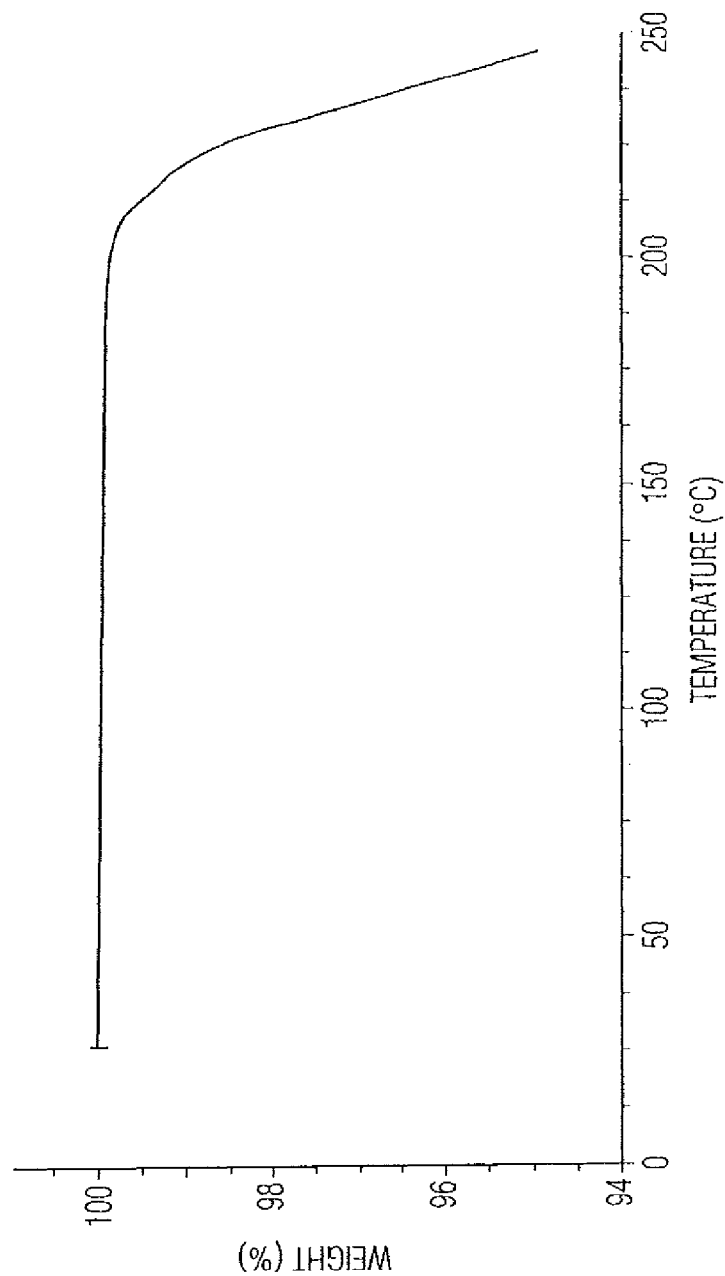
FIG. 3 is an illustration of thermogravimetric analysis (TGA) curve of crystalline anhydrate Form A of the dihydrogen phosphate salt of sitagliptin.

Also, Form A may be characterized by thermo gravimetric analysis (TGA) curve corresponding to a weight loss of about 0.038% (0.01082 mg) up to a temperature of about 100° C. (as shown in FIG. 3).

The present invention also includes processes for the preparation of Form A, which processes comprise the step of treating sitagliptin freebase with phosphoric acid in a solvent having a water content of less than about 6%.

The molar equivalents of phosphoric acid may be less than about 2.0, or less than about 1.0, or less than about 0.5 molar equivalents with respect to sitagliptin free base. The solvent may be aqueous isopropanol with a concentration of water within the solvent of less than about 6%.

Sitagliptin freebase may be taken in a suitable solvent, to which phosphoric acid may be added. The contents may be stirred at a higher temperature, such as about 70° C. The contents may be cooled to about 30° C. The separated solid may be isolated by conventional techniques, such as decantation, centrifugation, gravity filtration, suction filtration, or other techniques known in the art for the recovery of solids. The resulting product may be optionally dried. Drying may be carried out in a tray dryer, vacuum oven, air oven, fluidized bed drier, spin flash dryer, flash dryer, and the like. The drying may be carried out at a temperature of less than about 100° C., or less than about 90° C., or less than about 60° C., or any other suitable temperature at atmospheric pressure or under reduced pressure. The drying can be carried out for any desired time ranging from about 1 to 20 hours or longer.

In addition to Form A, the present invention includes the sulfuric acid, hydrobromic acid, methanesulfonic acid, acetic acid, benzoic acid, oxalic acid, succinic acid, mandelic acid, fumaric acid, and lactic acid salts of sitagliptin, which salts may be in crystalline form, and which may be made by the processes of the present invention.

Figure 4:
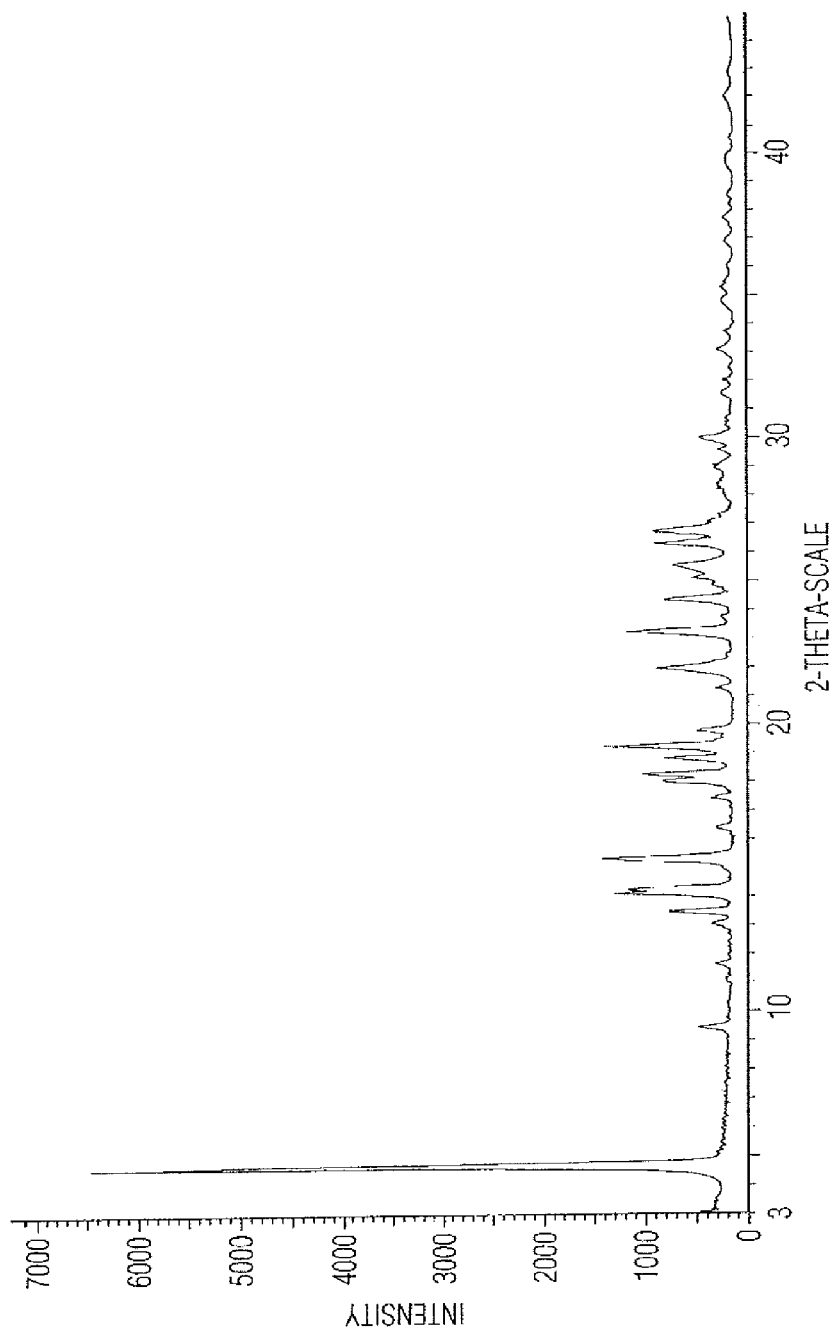
FIG. 4 is an illustration of powder X-ray diffraction ("PXRD") pattern of crystalline sitagliptin sulfate prepared according to example 14.
Figure 5:
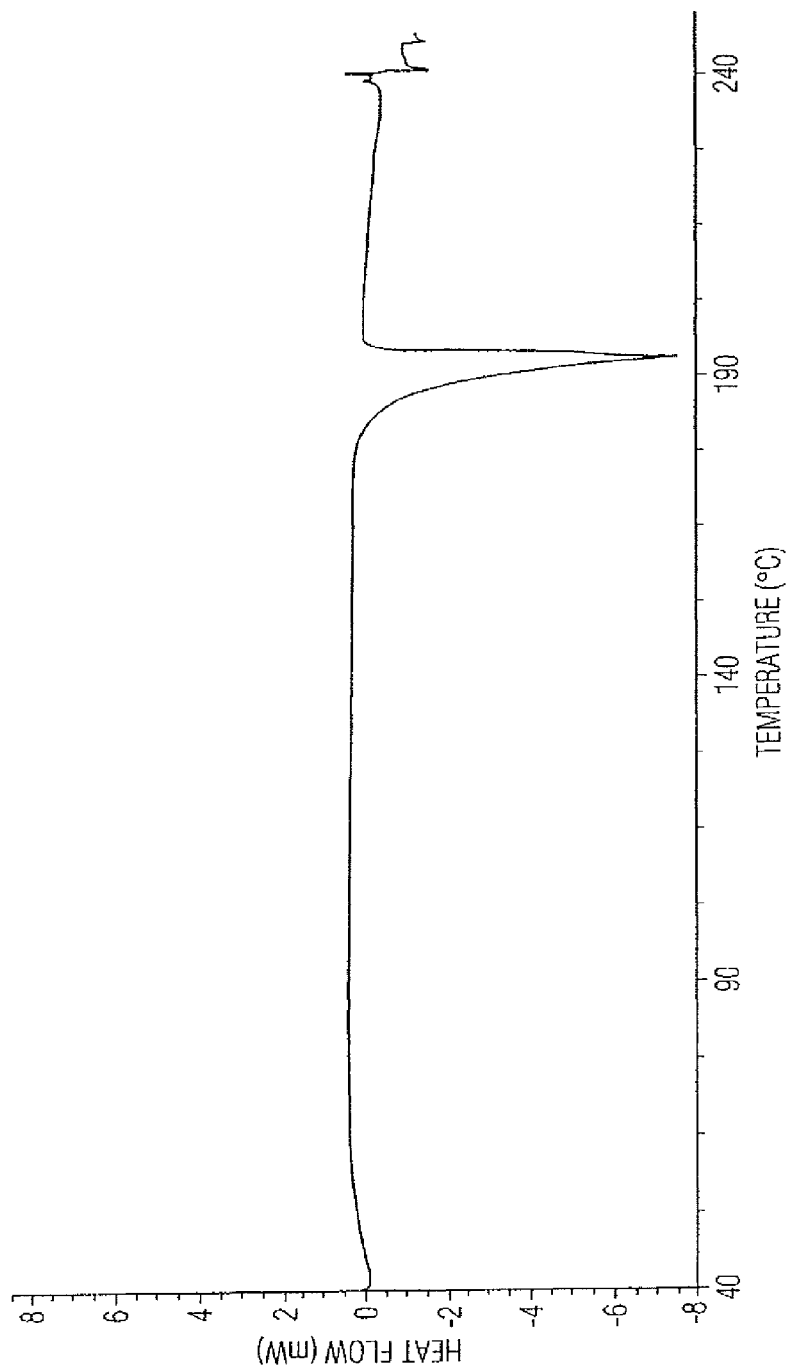
FIG. 5 is an illustration of differential scanning calorimetry ("DSC") curve of crystalline sitagliptin sulfate prepared according to example 14.
Figure 6:
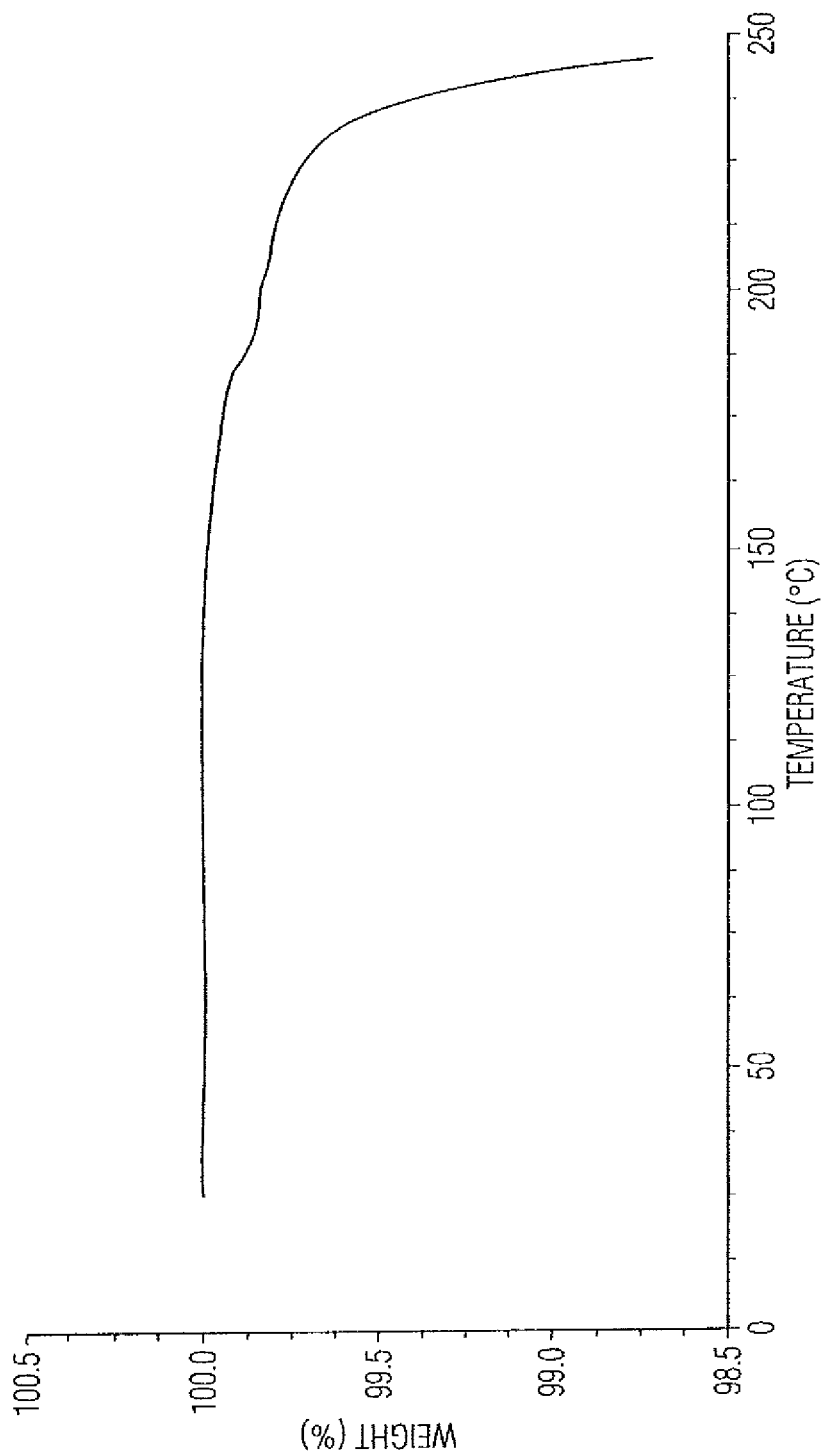
FIG. 6 is an illustration of thermogravimetric analysis ("TGA") curve of crystalline sitagliptin sulfate prepared according to example 14.

For example, there is provided crystalline sitagliptin sulfate having PXRD characteristic peaks at approximately 4.63, 14.06, 14.20, 15.30, 17.98, 18.23, 18.79, 19.23, 21.95, 23.23, 26.29 and 26.73±0.2 degrees 2 theta. The crystalline sitagliptin sulfate may be characterized by an PXRD pattern substantially as shown in FIG. 4. Crystalline sitagliptin sulfate may also be characterized by a DSC endotherm peak at about 192° C. The crystalline sitagliptin sulfate may be characterized by a DSC thermogram substantially as shown in FIG. 5. The crystalline sitagliptin sulfate may also be characterized by a TGA weight loss of about 0.0029%. The crystalline sitagliptin sulfate may be characterized by a TGA curve substantially as shown in FIG. 6.

Figure 7:
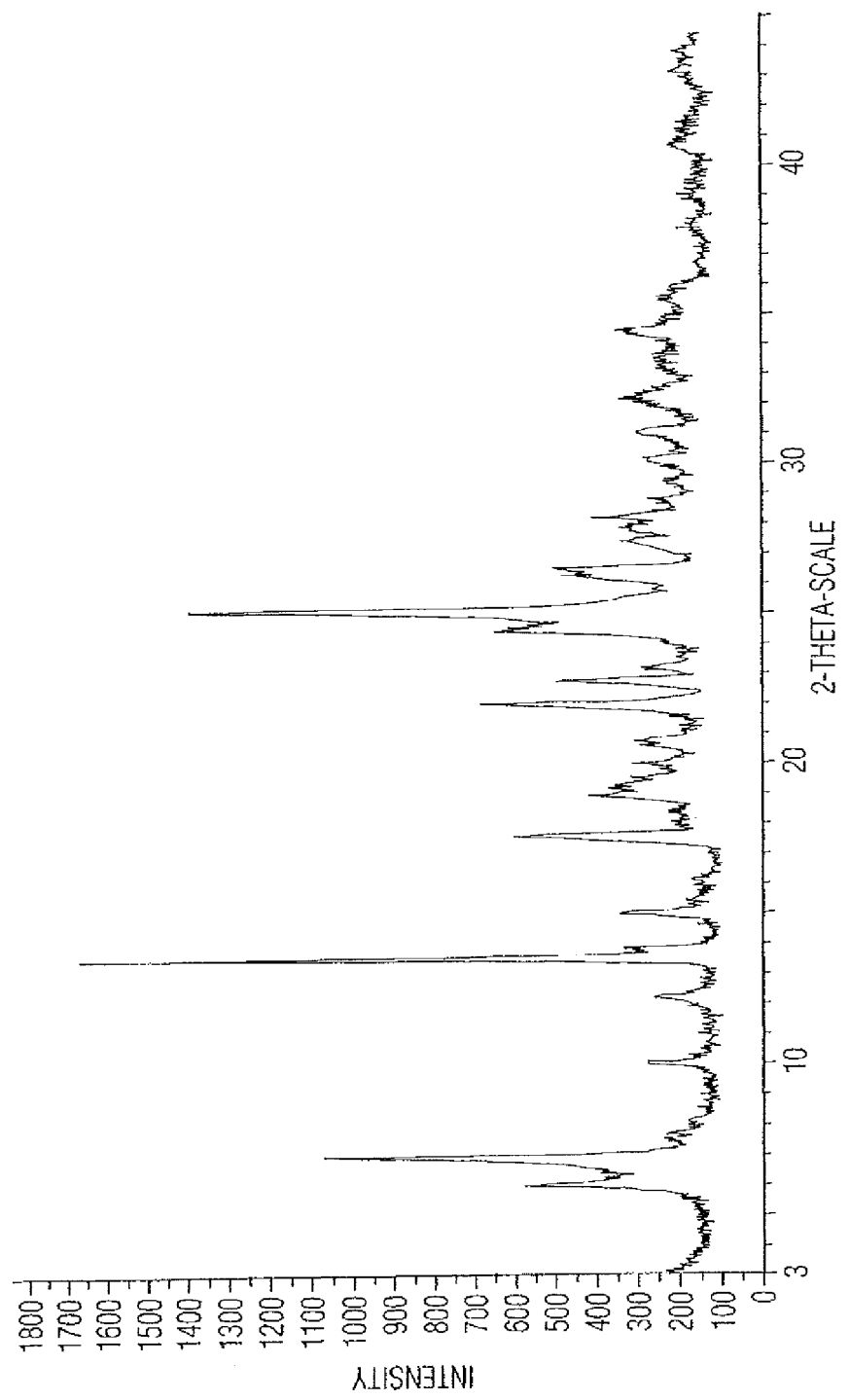
FIG. 7 is an illustration of PXRD pattern of crystalline sitagliptin hydrobromide prepared according to example 15.
Figure 8:
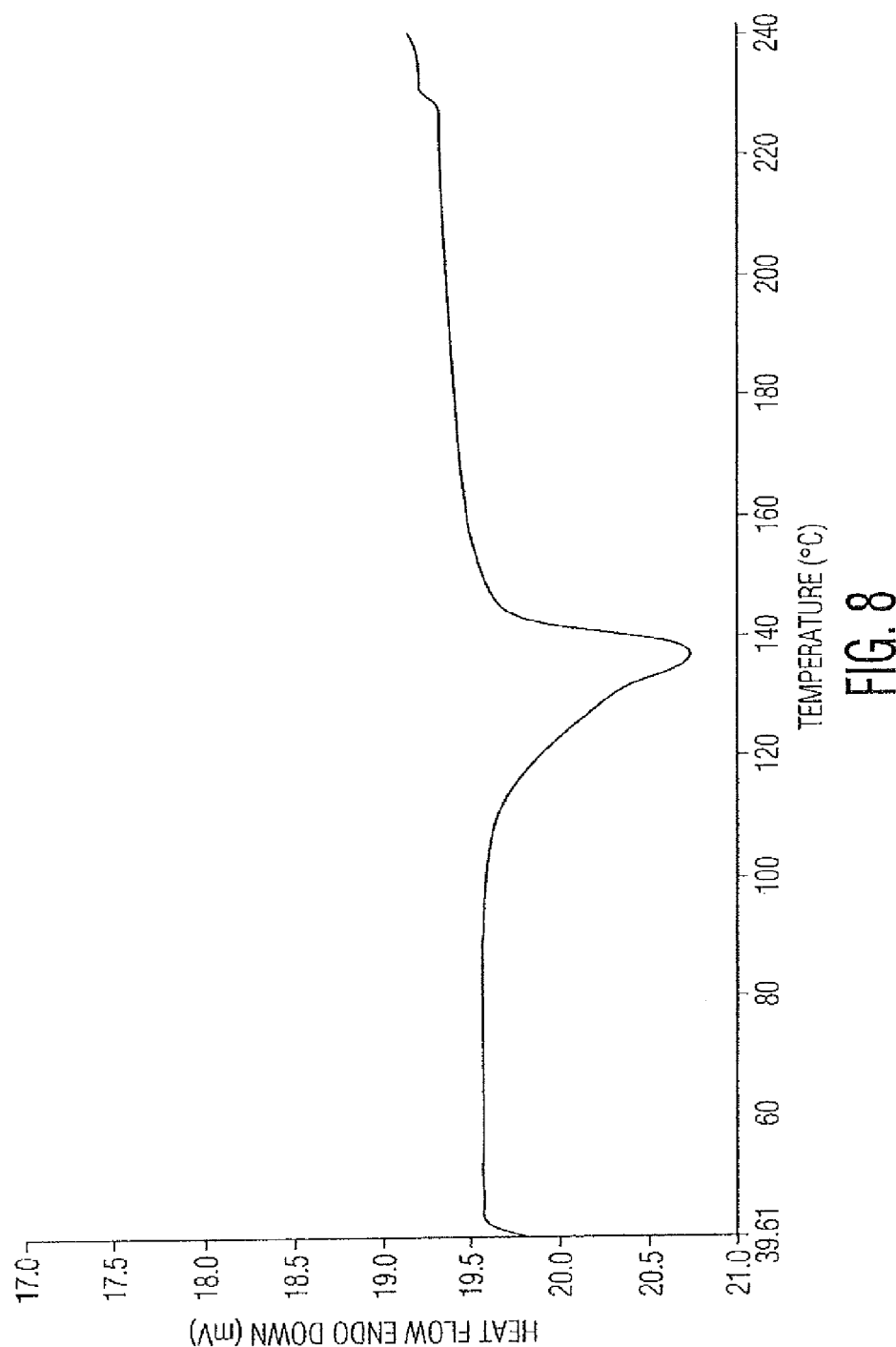
FIG. 8 is an illustration of DSC curve of crystalline sitagliptin hydrobromide prepared according to example 15.
Figure 9:
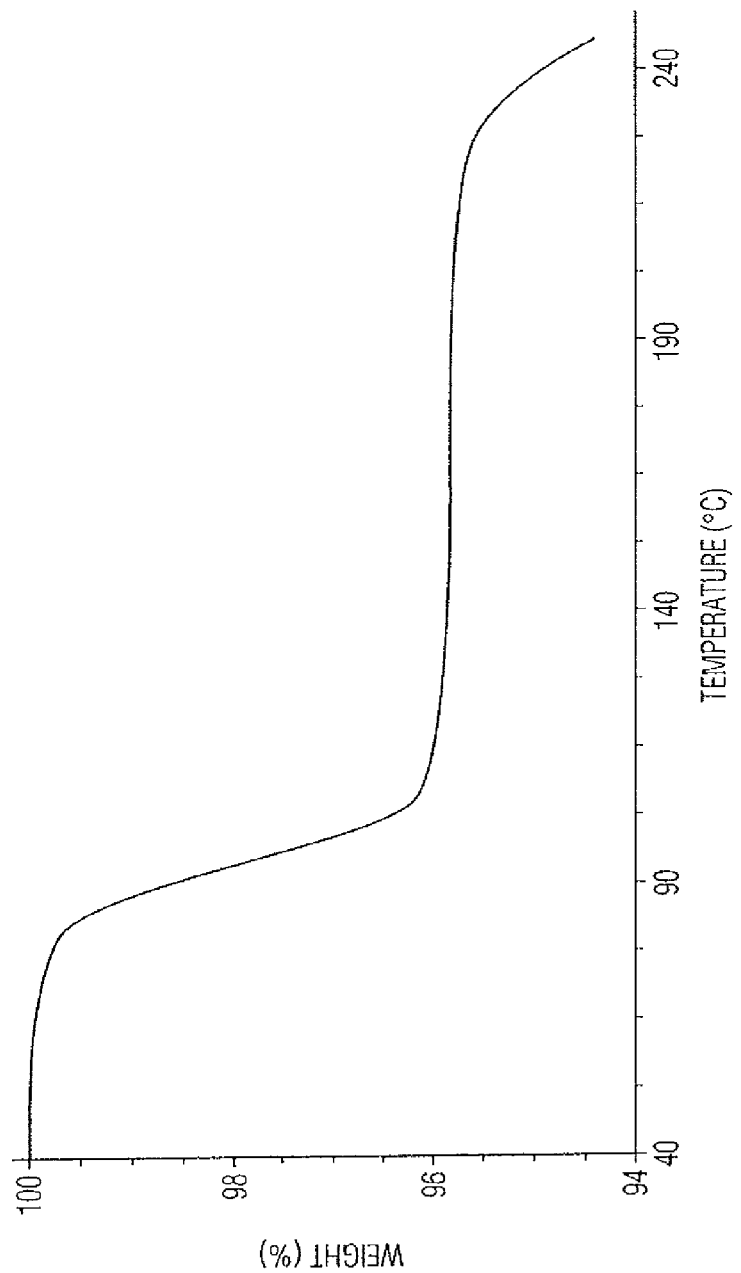
FIG. 9 is an illustration of TGA curve of crystalline sitagliptin hydrobromide prepared according to example 15.

For example, there is provided crystalline sitagliptin hydrobromide having PXRD characteristic peaks at approximately 5.92, 6.81, 13.45, 17.53, 21.88, 22.67, 24.39, 25.03 and 26.41±0.2 degrees 2 theta. The crystalline sitagliptin hydrobromide may be characterized by an PXRD pattern substantially as shown in FIG. 7. Crystalline sitagliptin hydrobromide may also be characterized by a DSC endotherm peak at about 137° C. The crystalline sitagliptin hydrobromide may be characterized by a DSC thermogram substantially as shown in FIG. 8. The crystalline sitagliptin hydrobromide may also be characterized by a TGA weight loss of about 4.178%. The crystalline sitagliptin hydrobromide may be characterized by a TGA curve substantially as shown by FIG. 9.

Figure 10:
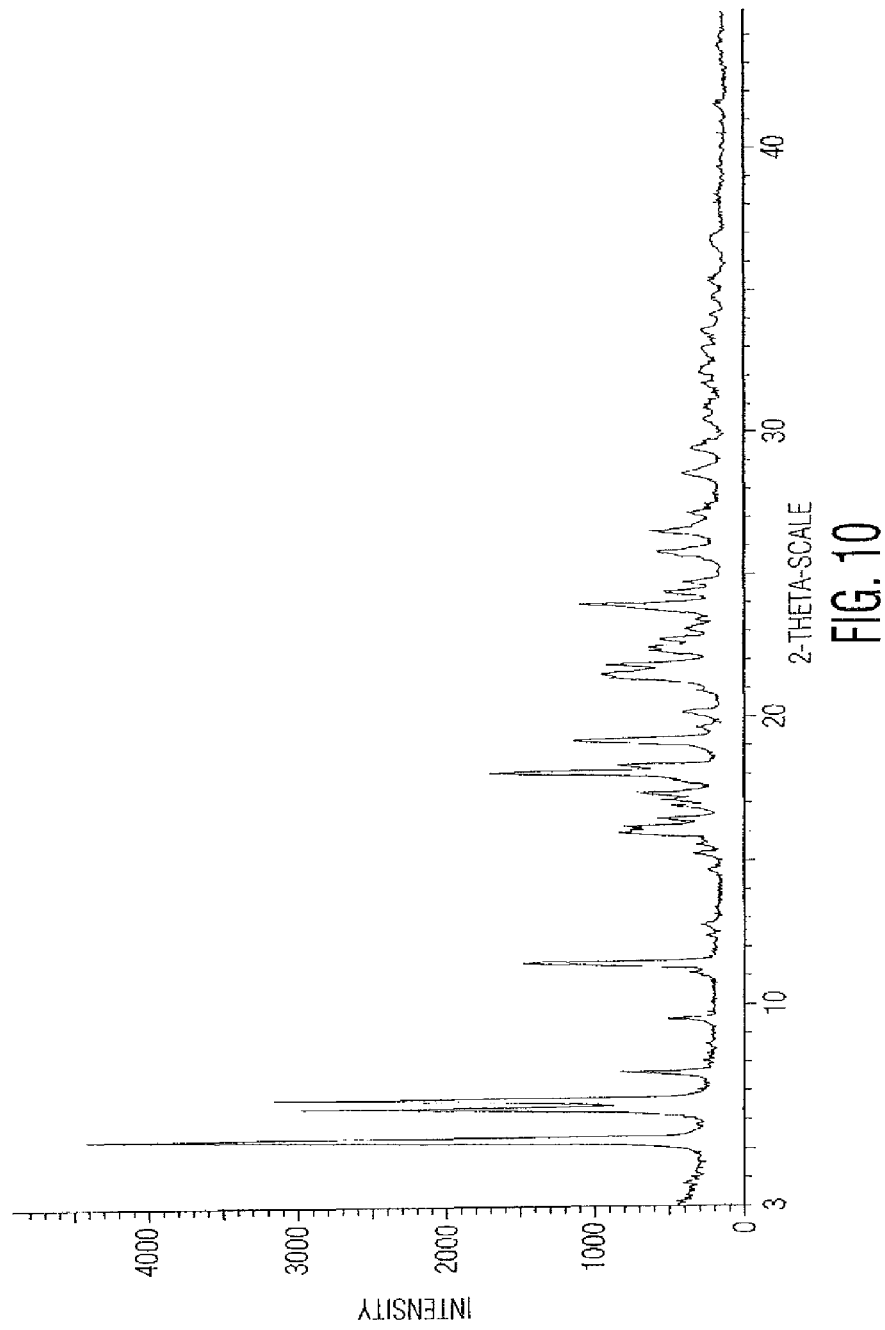
FIG. 10 is an illustration of PXRD pattern of crystalline sitagliptin methane sulfonate prepared according to example 16.
Figure 11:
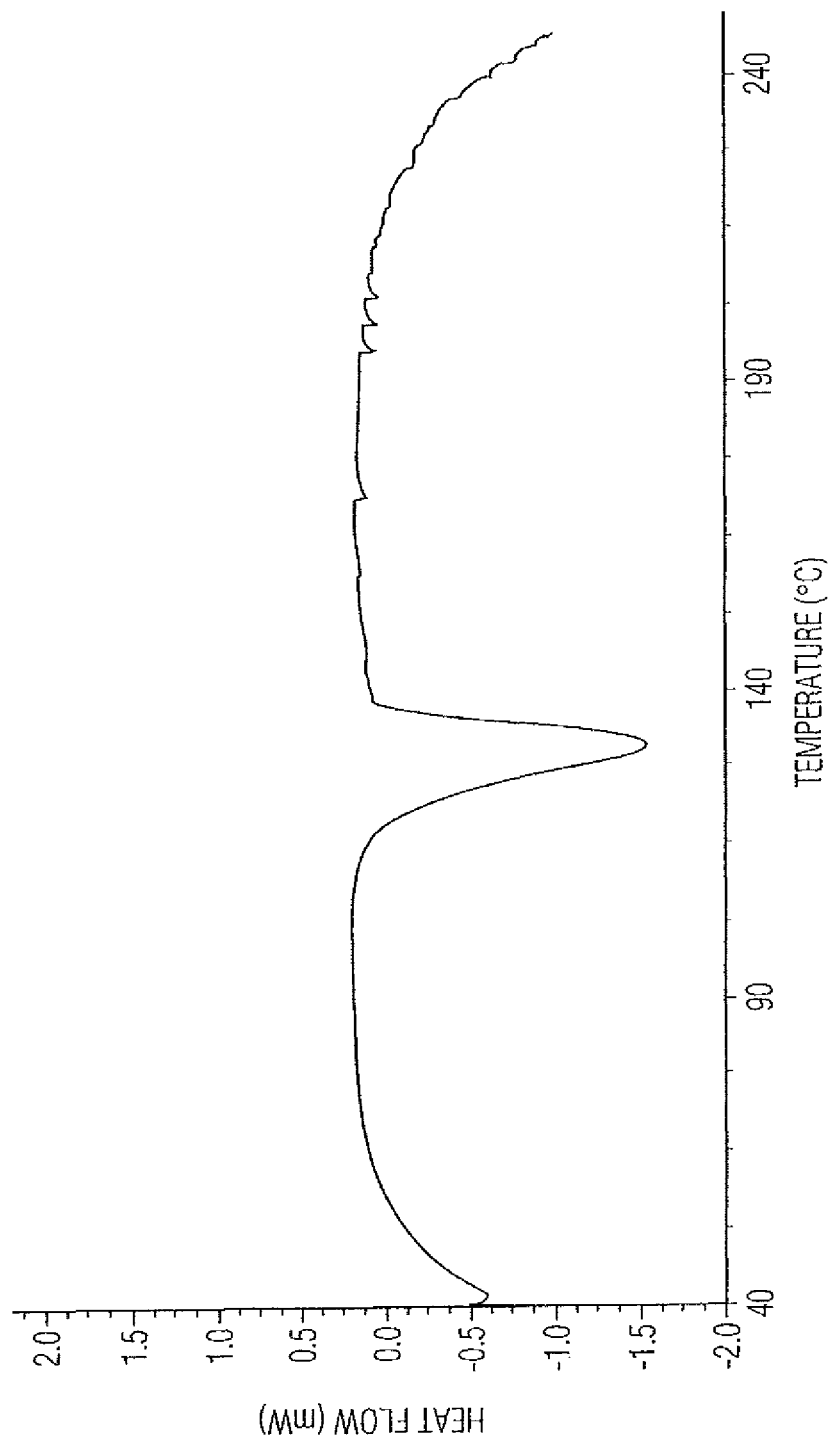
FIG. 11 is an illustration of DSC curve of crystalline sitagliptin methane sulfonate prepared according to example 16.
Figure 12:
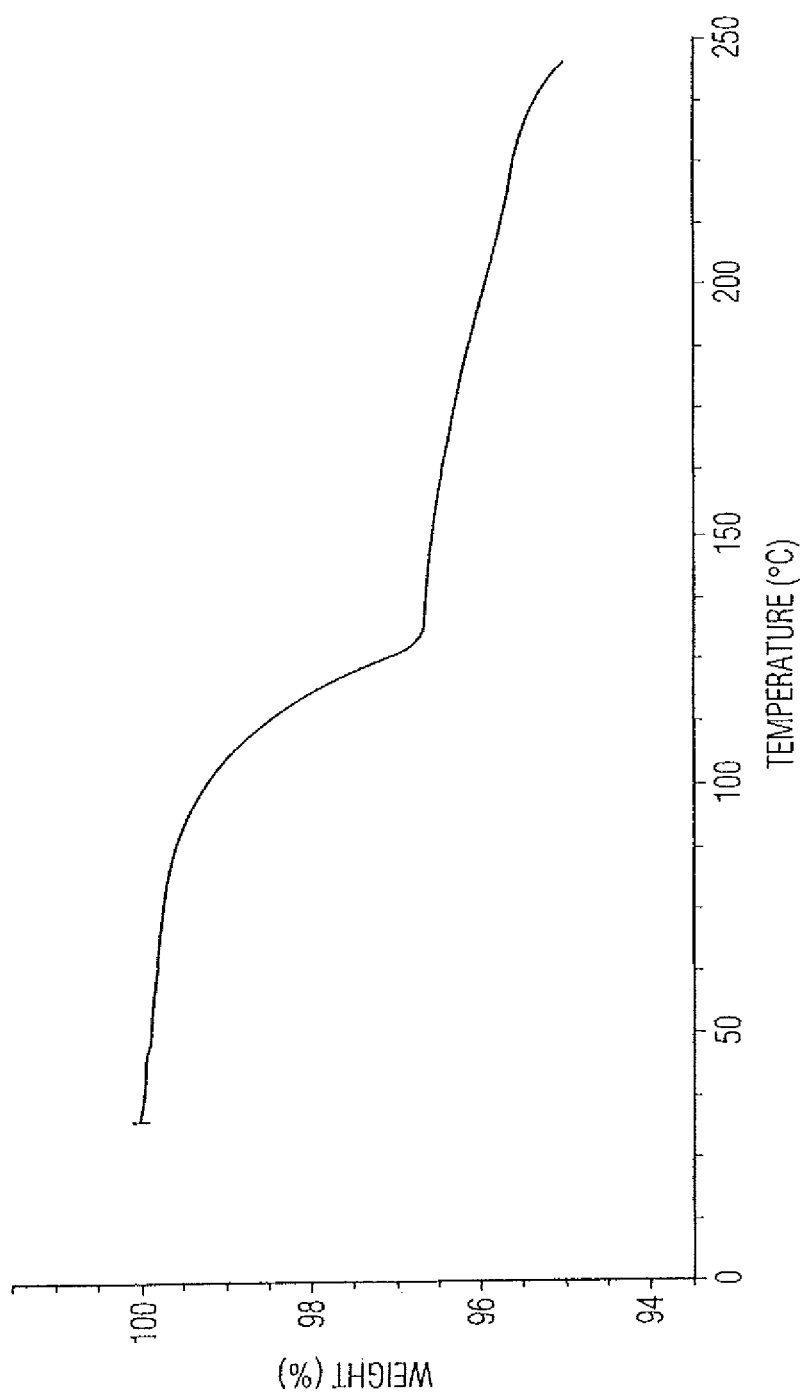
FIG. 12 is an illustration of TGA curve of crystalline sitagliptin methane sulfonate prepared according to example 16.

For example, there is provided crystalline sitagliptin methane sulfonate having PXRD characteristic peaks at approximately 5.25, 6.32, 6.62, 11.42, 18.01, 19.14 and 23.91±0.2 degrees 2 theta. The crystalline sitagliptin methane sulfonate may be characterized by an PXRD pattern substantially as shown in FIG. 10. Crystalline sitagliptin methane sulfonate may also be characterized by a DSC endotherm peak at about 131° C. The crystalline sitagliptin methane sulfonate may be characterized by a DSC thermogram substantially as shown in FIG. 11. The crystalline sitagliptin methane sulfonate may also be characterized by a TGA weight loss of about 3.386%. The crystalline sitagliptin methane sulfonate may be characterized by a TGA curve substantially as shown by FIG. 12.

Figure 13:
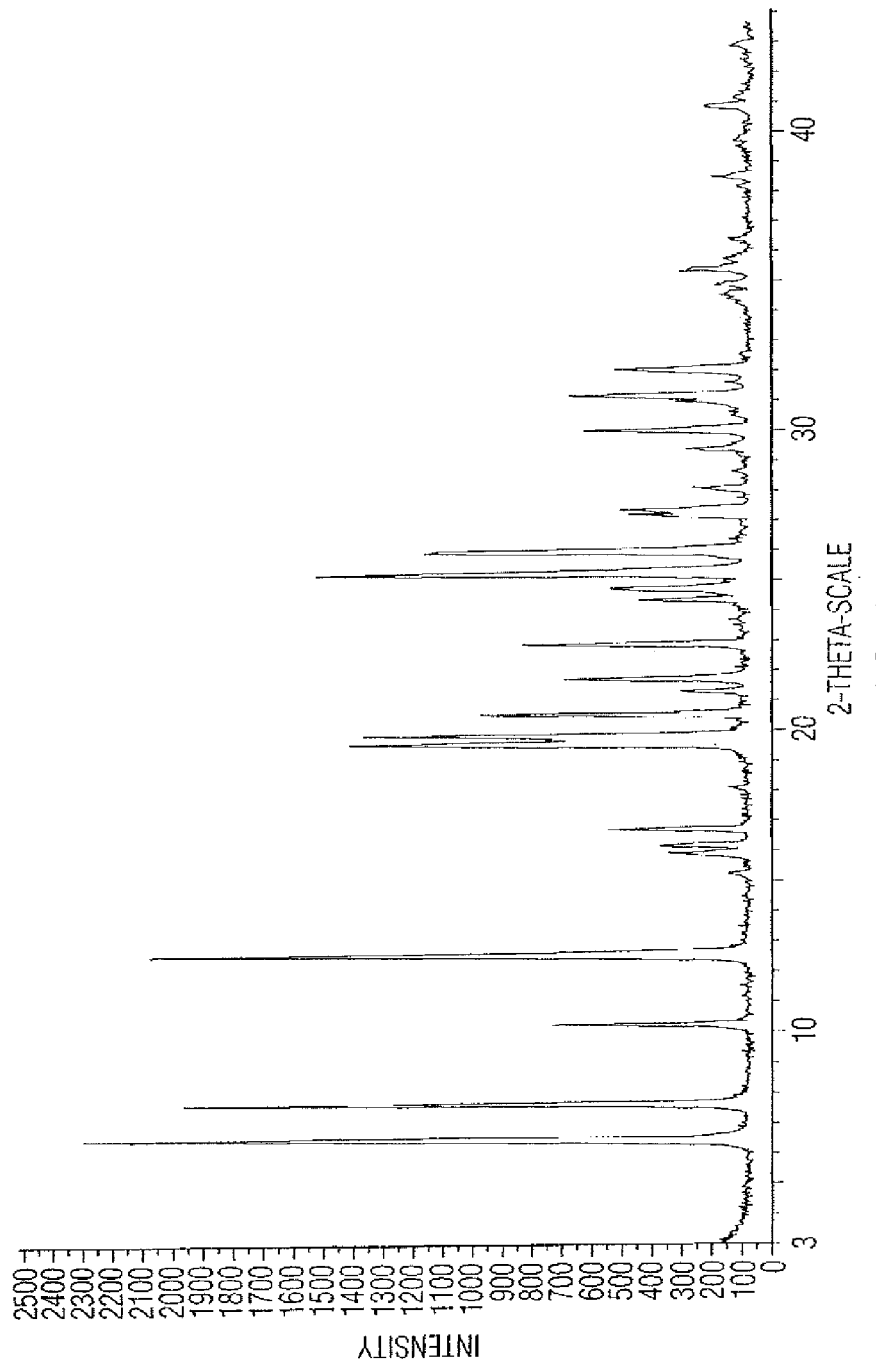
FIG. 13 is an illustration of PXRD pattern of crystalline sitagliptin acetate prepared according to example 17.
Figure 14:
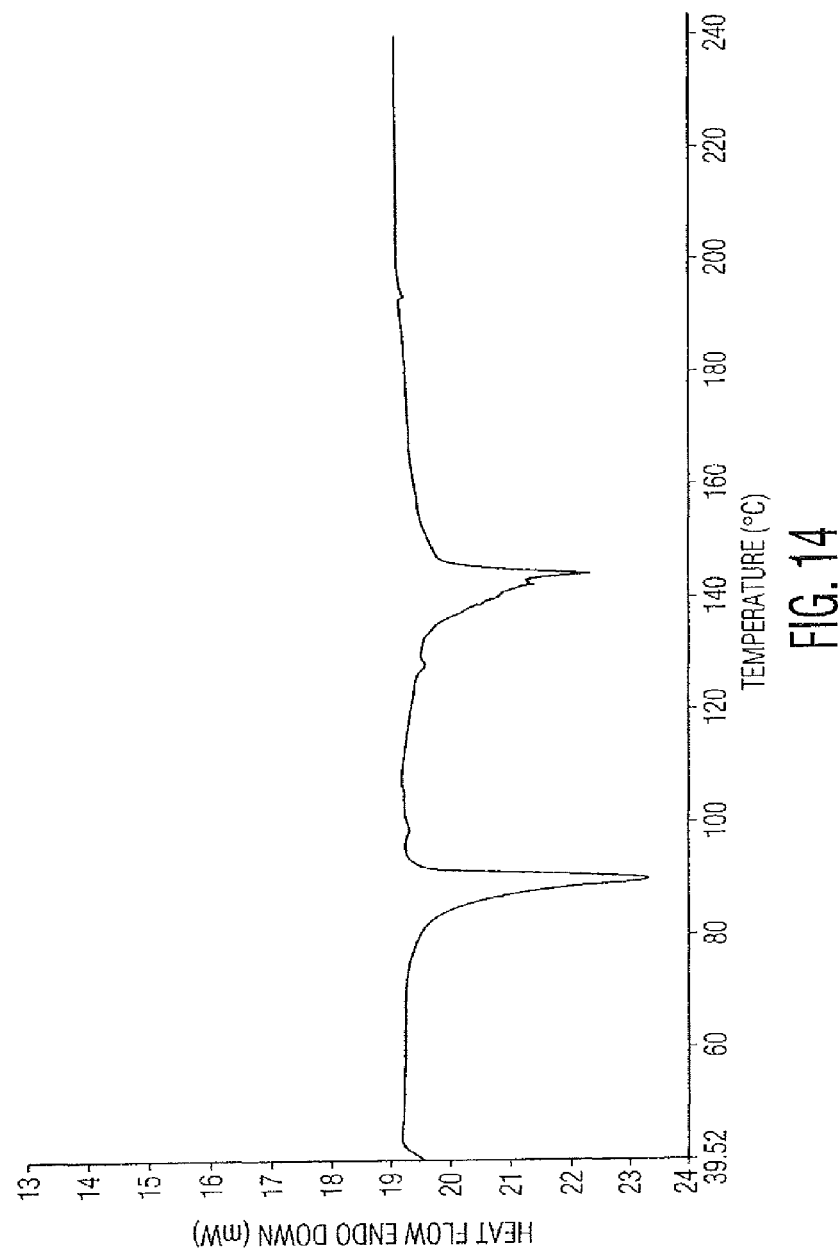
FIG. 14 is an illustration of DSC curve of crystalline sitagliptin acetate prepared according to example 17.
Figure 15:
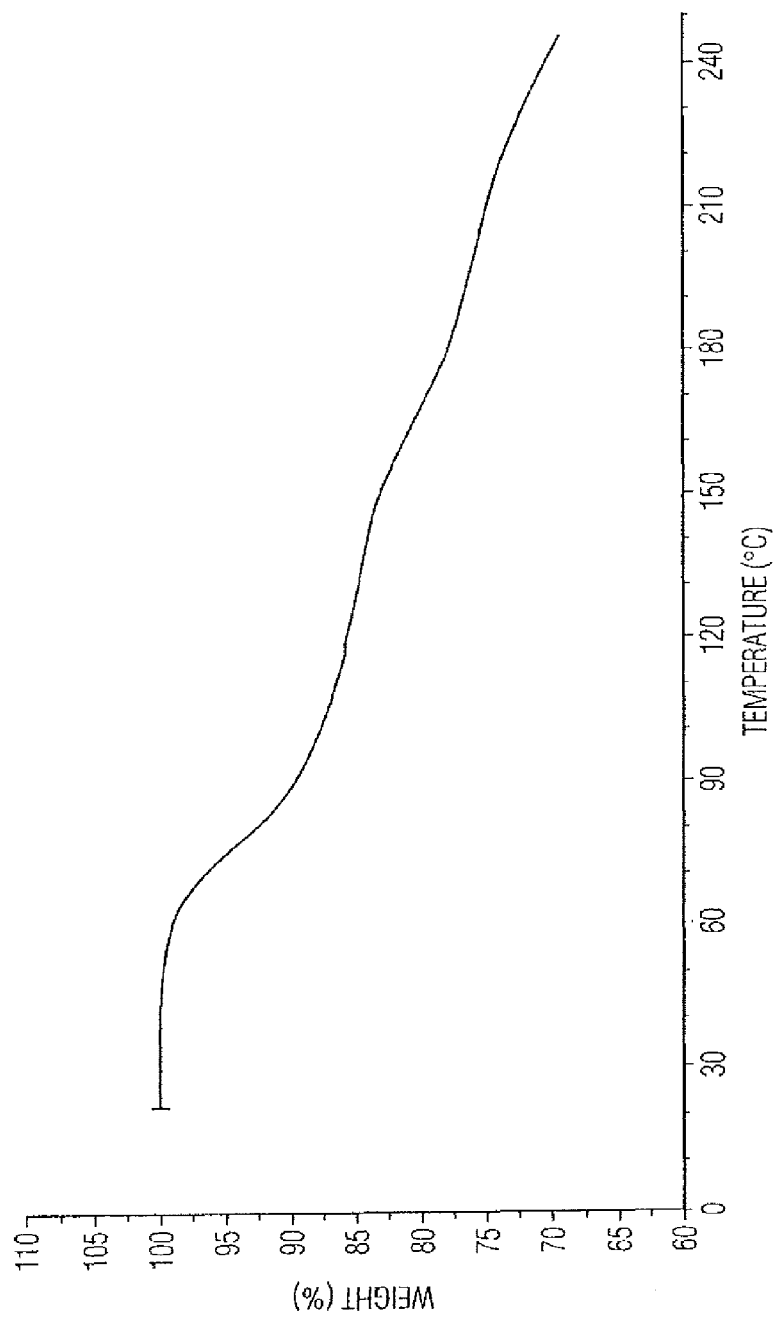
FIG. 15 is an illustration of TGA curve of crystalline sitagliptin acetate prepared according to example 17.

For example, there is provided crystalline sitagliptin acetate having PXRD characteristic peaks at approximately 6.42, 7.61, 10.25, 12.58, 19.51, 19.80, 20.54, 22.89, 25.26 and 25.98±0.2 degrees 2 theta. The crystalline sitagliptin acetate may be characterized by an PXRD pattern substantially as shown in FIG. 13. Crystalline sitagliptin acetate may also be characterized by a DSC endotherm peak at about 144° C. The crystalline sitagliptin acetate may be characterized by a DSC thermogram substantially as shown in FIG. 14. The crystalline sitagliptin acetate may also be characterized by a TGA weight loss of about 14.16%. The crystalline sitagliptin acetate may be characterized by a TGA curve substantially as shown by FIG. 15.

Figure 16:
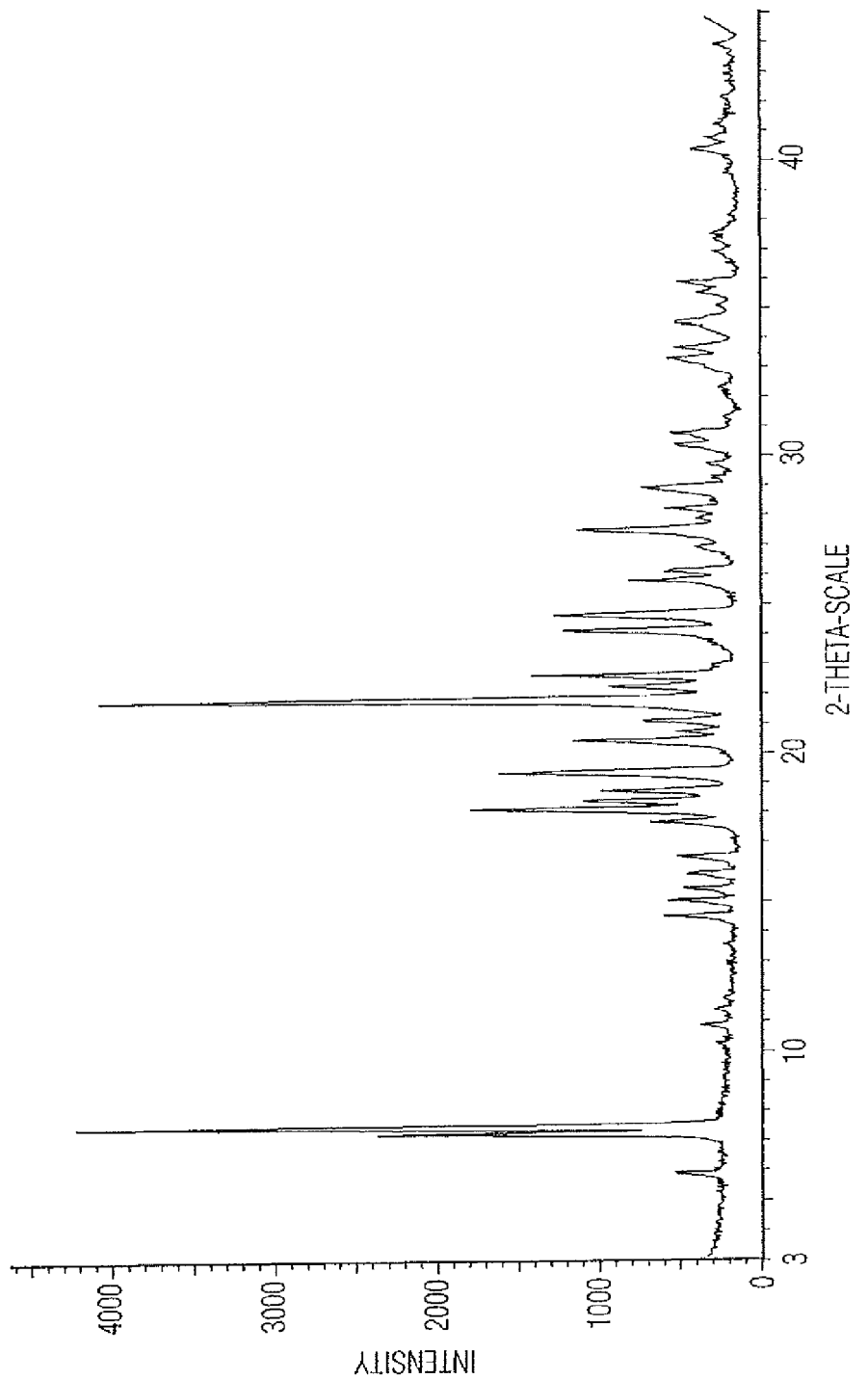
FIG. 16 is an illustration of PXRD pattern of crystalline sitagliptin benzoate prepared according to example 18.
Figure 17:
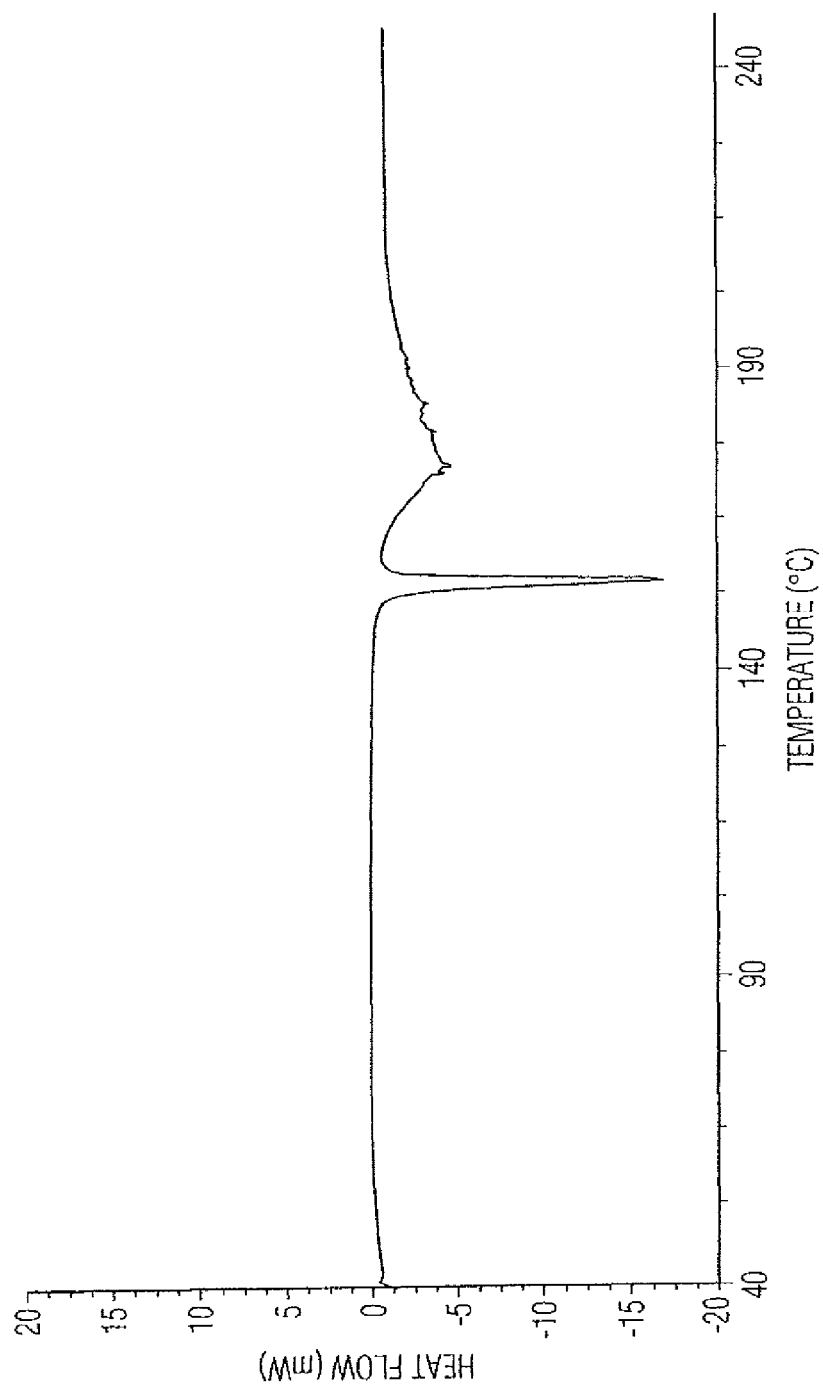
FIG. 17 is an illustration of DSC curve of crystalline sitagliptin benzoate prepared according to example 18.
Figure 18:
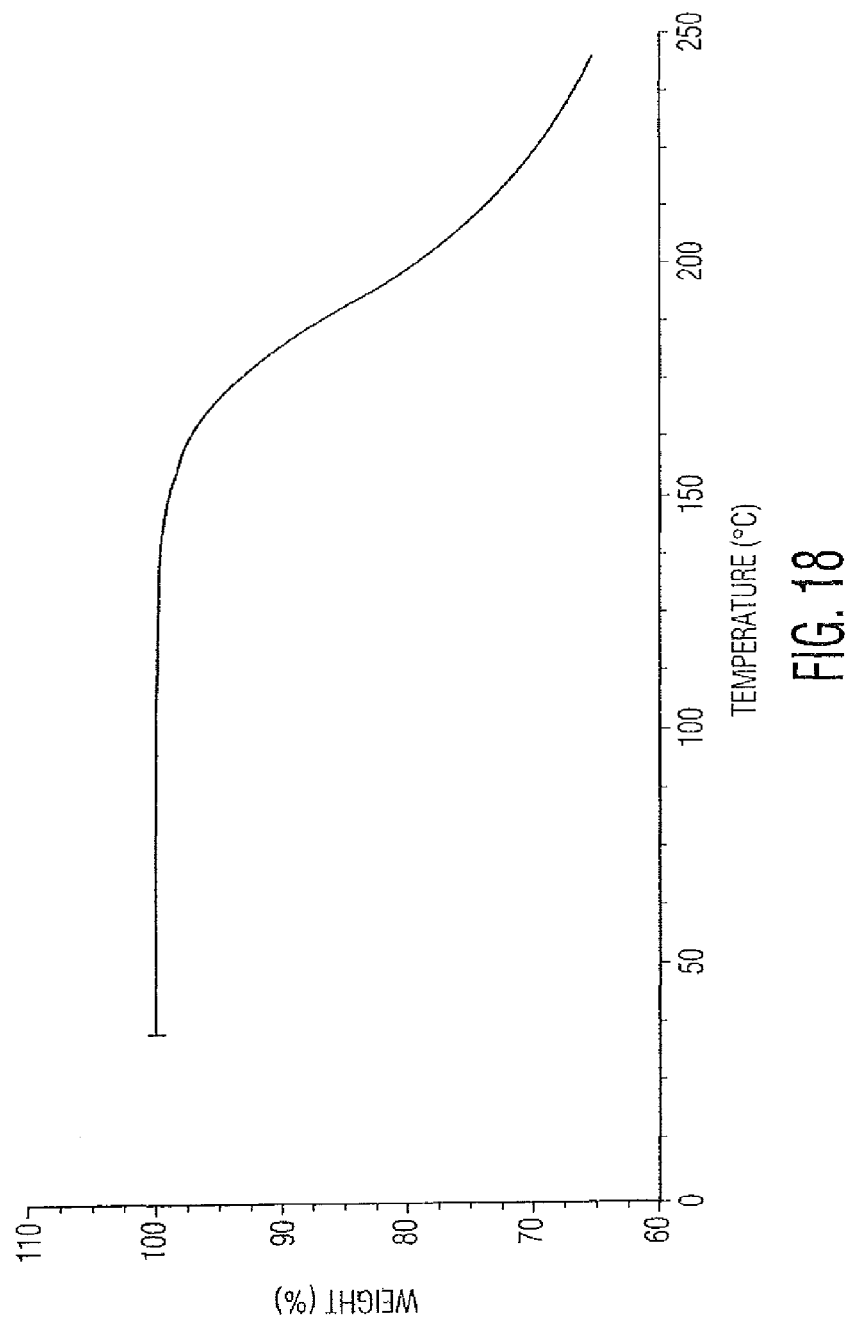
FIG. 18 is an illustration of TGA curve of crystalline sitagliptin benzoate prepared according to example 18.

For example, there is provided crystalline sitagliptin benzoate having PXRD characteristic peaks at approximately 7.19, 7.45, 18.11, 18.38, 19.35, 20.42, 21.81, 22.61, 24.11, 24.63 and 27.51±0.2 degrees 2 theta. The crystalline sitagliptin benzoate may be characterized by an PXRD pattern substantially as shown in FIG. 16. Crystalline sitagliptin benzoate may also be characterized by a DSC endotherm peak at about 155° C. The crystalline sitagliptin benzoate may be characterized by a DSC thermogram substantially as shown in FIG. 17. The crystalline sitagliptin benzoate may also be characterized by a TGA weight loss of about 0.1163%. The crystalline sitagliptin benzoate may be characterized by a TGA curve substantially as shown by FIG. 18.

Figure 19:
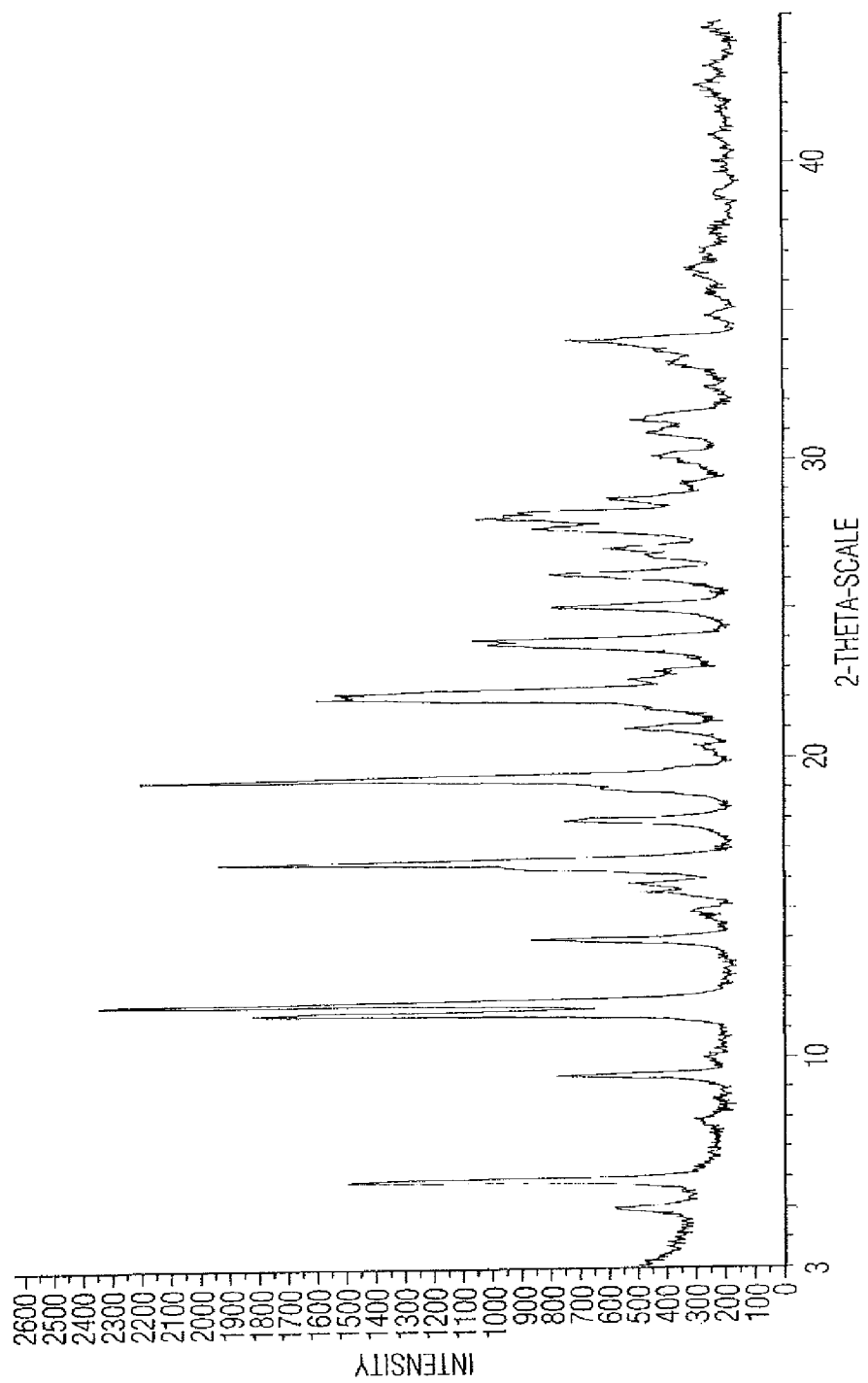
FIG. 19 is an illustration of PXRD pattern of crystalline sitagliptin oxalate prepared according to example 19.
Figure 20:
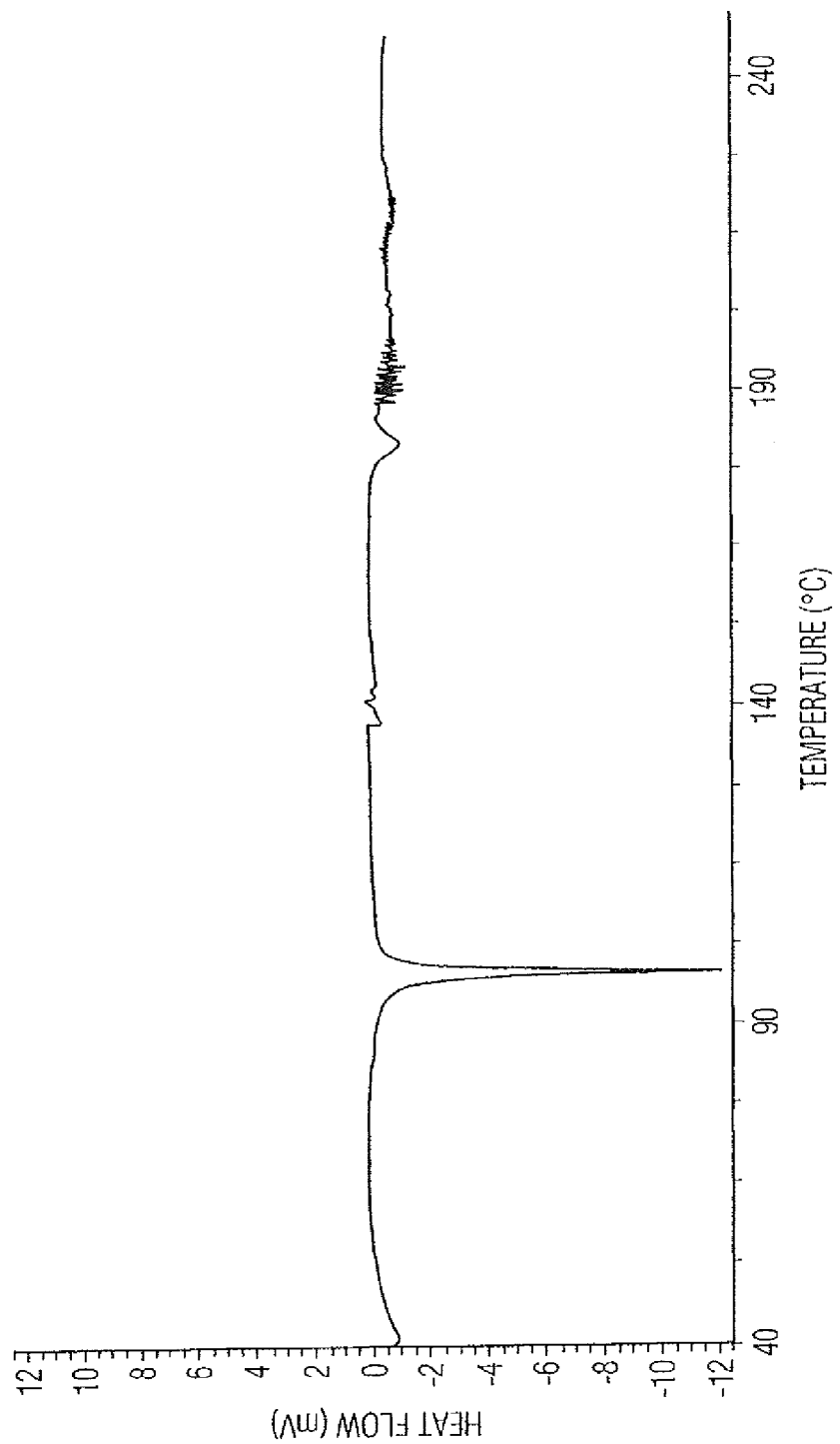
FIG. 20 is an illustration of DSC curve of crystalline sitagliptin oxalate prepared according to example 19.
Figure 21:
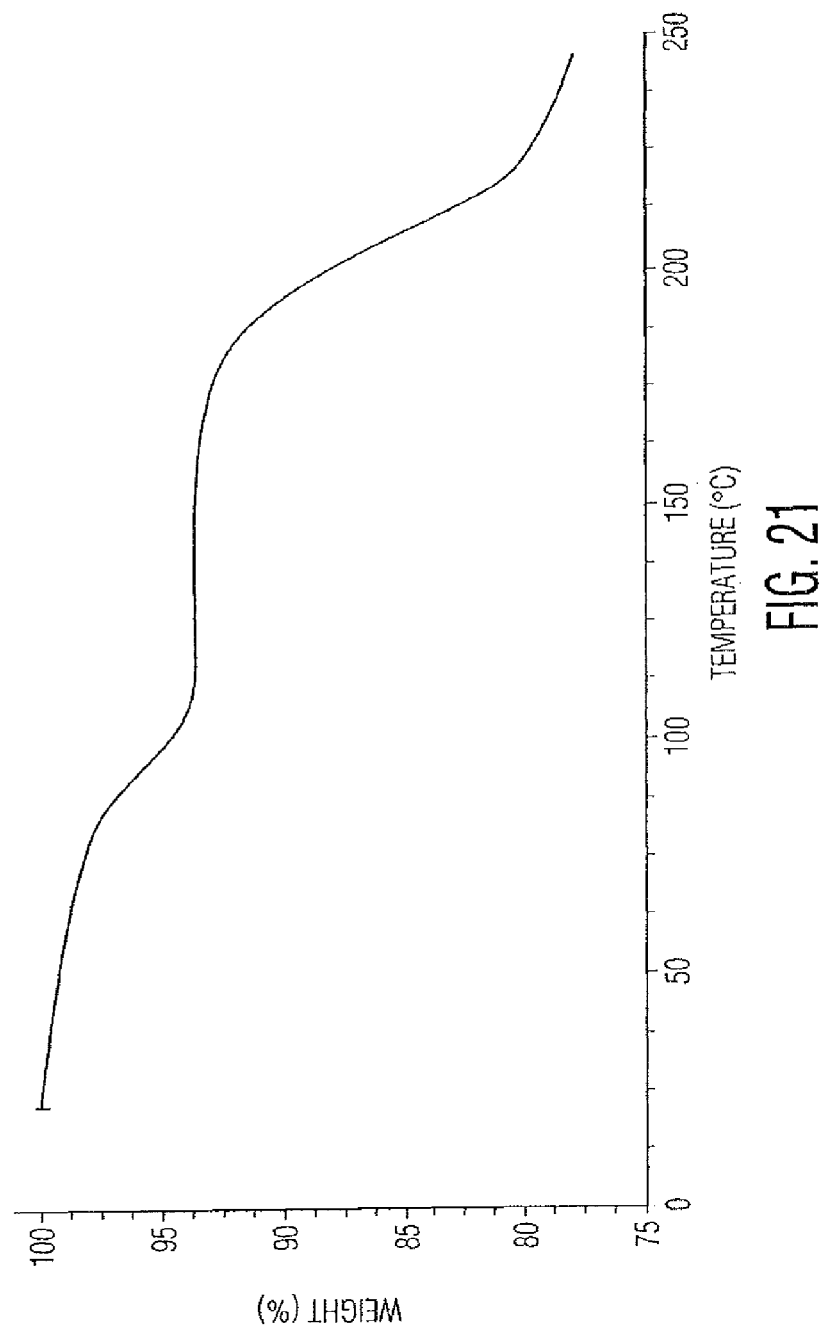
FIG. 21 is an illustration of TGA curve of crystalline sitagliptin oxalate prepared according to example 19.

For example, there is provided crystalline sitagliptin oxalate having PXRD characteristic peaks at approximately 5.92, 11.54, 11.92, 14.00, 16.39, 16.64, 19.40, 22.21, 24.00, 28.11 and 28.26±0.2 degrees 2 theta. The crystalline sitagliptin oxalate may be characterized by an PXRD pattern substantially as shown in FIG. 19. Crystalline sitagliptin oxalate may also be characterized by a DSC endotherm peak at about 98° C. The crystalline sitagliptin oxalate may be characterized by a DSC thermogram substantially as shown in FIG. 20. The crystalline sitagliptin oxalate may also be characterized by a TGA weight loss of about 6.245%. The crystalline sitagliptin oxalate may be characterized by a TGA curve substantially as shown by FIG. 21.

For example, there is provided crystalline sitagliptin succinate having PXRD characteristic peaks at approximately 13.06, 13.50, 15.73, 17.04, 17.35, 17.57, 20.15, 24.35, 25.15, 25.76 and 26.35±0.2 degrees 2 theta. The crystalline sitagliptin succinate may be characterized by an PXRD pattern substantially as shown in FIG. 19. Crystalline sitagliptin succinate may also be characterized by a DSC endotherm peak at about 120° C. The crystalline sitagliptin succinate may be characterized by a DSC thermogram substantially as shown in FIG. 20. The crystalline sitagliptin succinate may also be characterized by a TGA weight loss of about 0.8623%. The crystalline sitagliptin succinate may be characterized by a TGA curve substantially as shown by FIG. 21.

Figure 22:
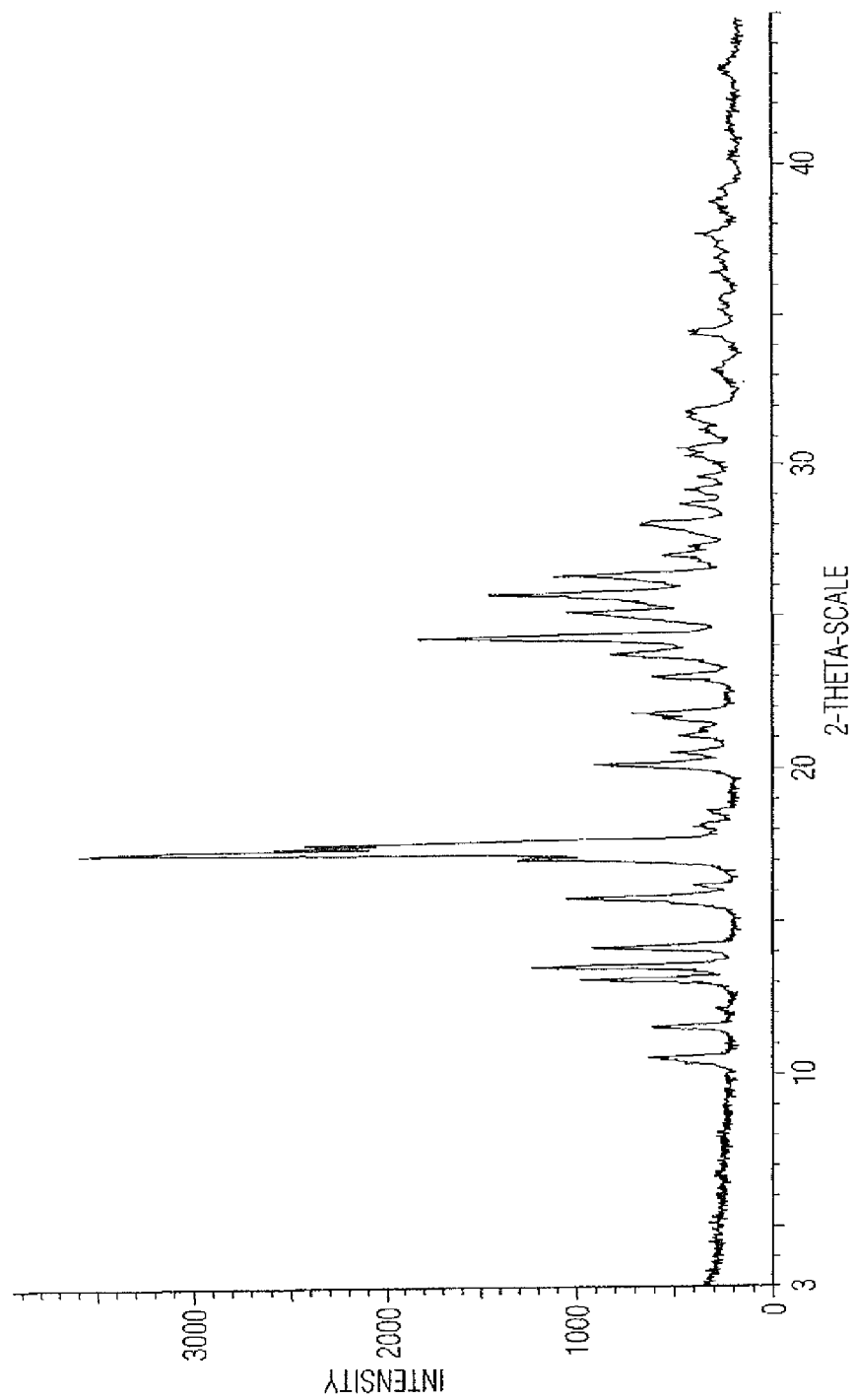
FIG. 22 is an illustration of PXRD pattern of crystalline sitagliptin succinate prepared according to example 20.
Figure 23:
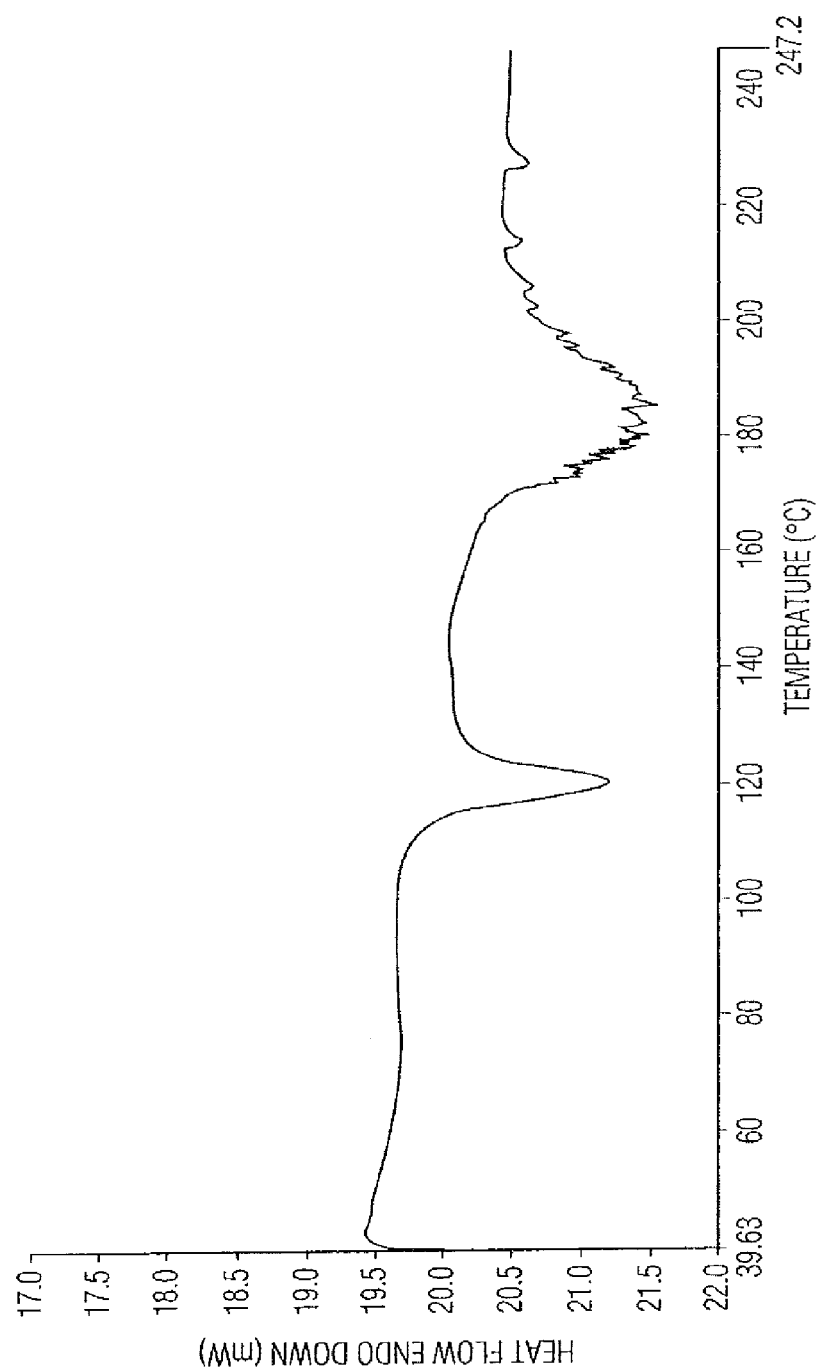
FIG. 23 is an illustration of DSC curve of crystalline sitagliptin succinate prepared according to example 20.
Figure 24:
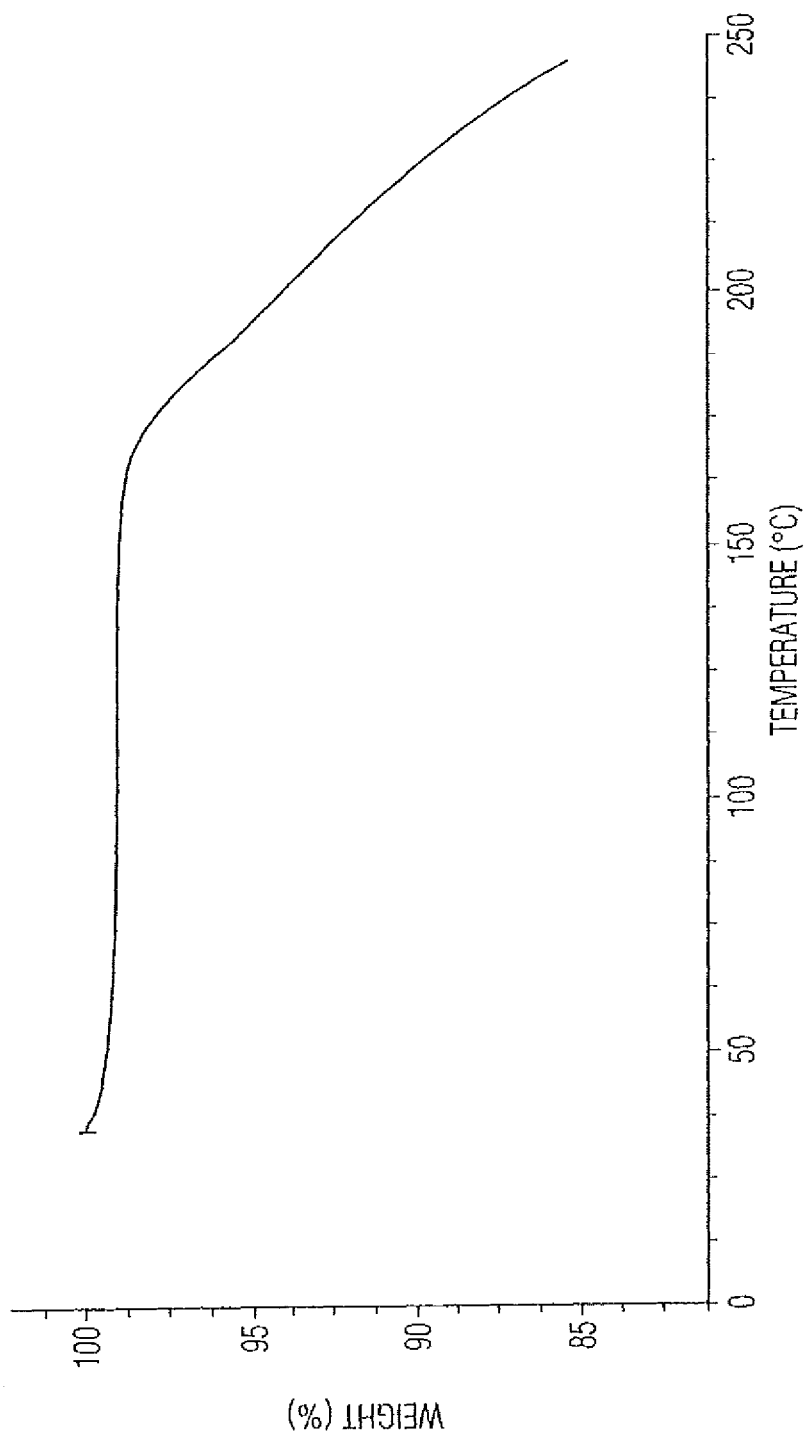
FIG. 24 is an illustration of TGA curve of crystalline sitagliptin succinate prepared according to example 20.

For example, there is provided crystalline sitagliptin mandelate having PXRD characteristic peaks at approximately 5.45, 6.02, 7.47, 10.60, 14.33, 15.88, 17.35, 17.60, 19.02, 21.98, 22.63 and 25.04±0.2 degrees 2 theta. The crystalline sitagliptin mandelate may be characterized by an PXRD pattern substantially as shown in FIG. 22. Crystalline sitagliptin mandelate may also be characterized by a DSC endotherm peak at about 169° C. The crystalline sitagliptin mandelate may be characterized by a DSC thermogram substantially as shown in FIG. 23. The crystalline sitagliptin mandelate may also be characterized by a TGA weight loss of about 0.149%. The crystalline sitagliptin mandelate may be characterized by a TGA curve substantially as shown by FIG. 24.

Figure 25:
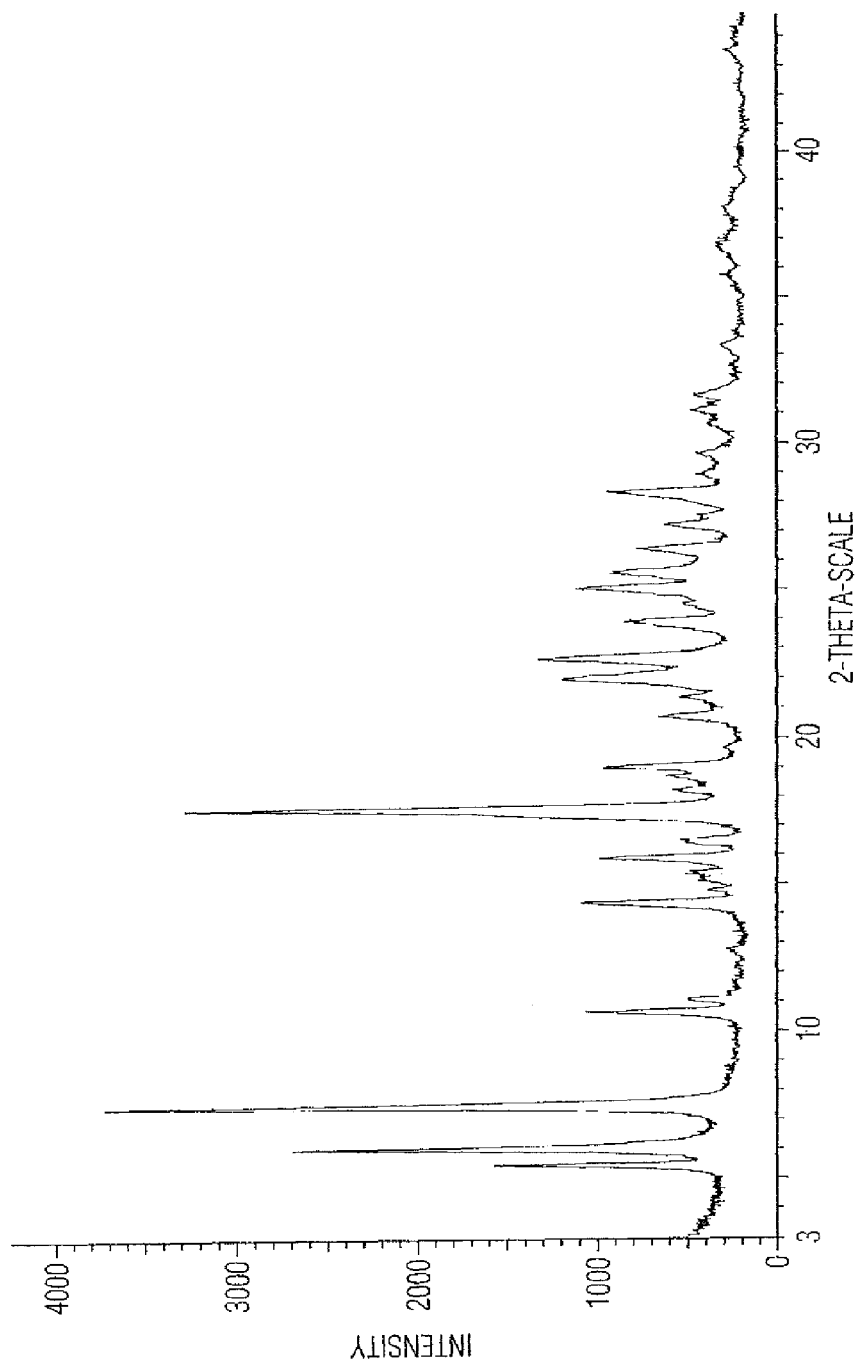
FIG. 25 is an illustration of PXRD pattern of crystalline sitagliptin mendelate prepared according to example 21.
Figure 26:
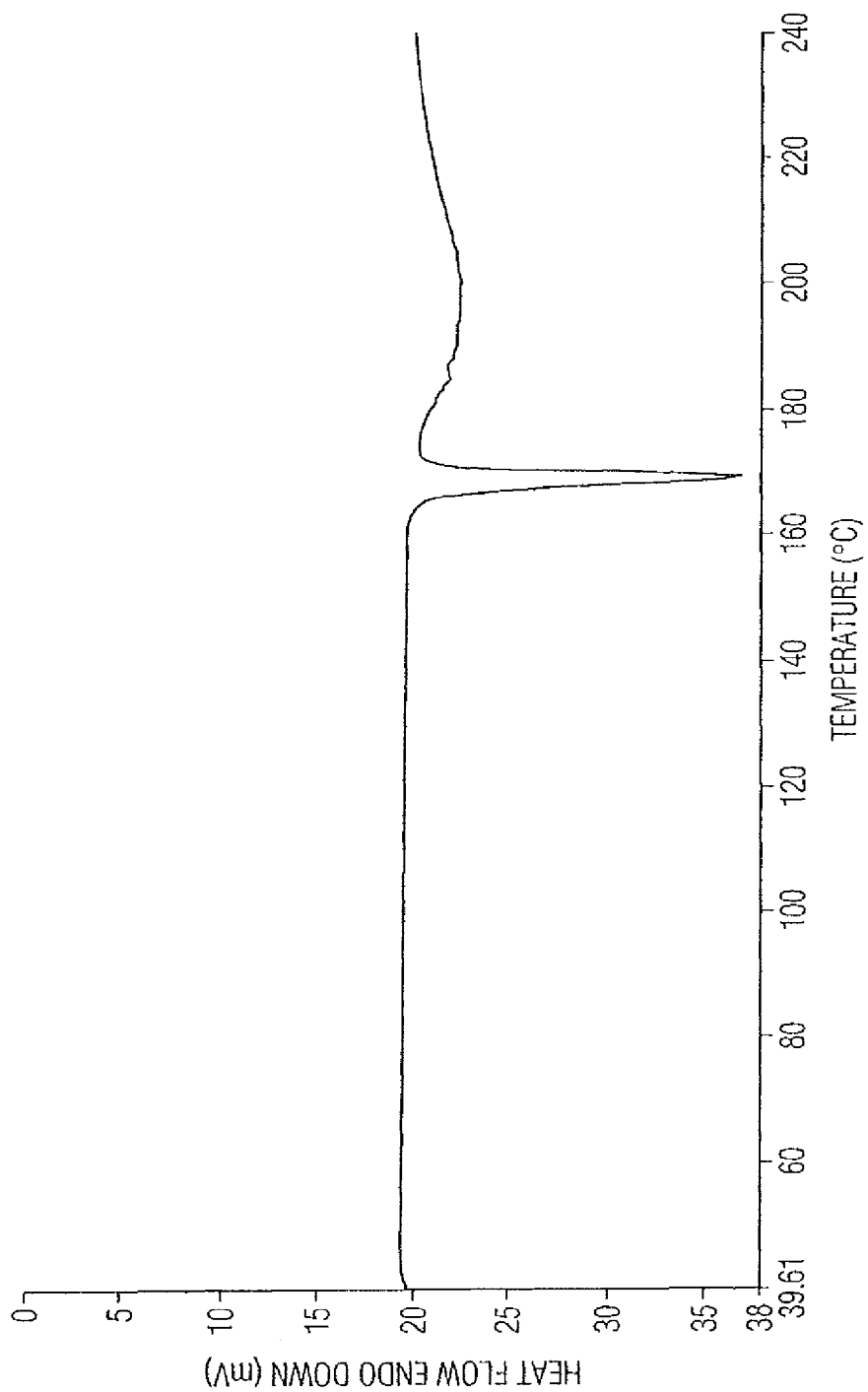
FIG. 26 is an illustration of DSC curve of crystalline sitagliptin mendelate prepared according to example 21.
Figure 27:
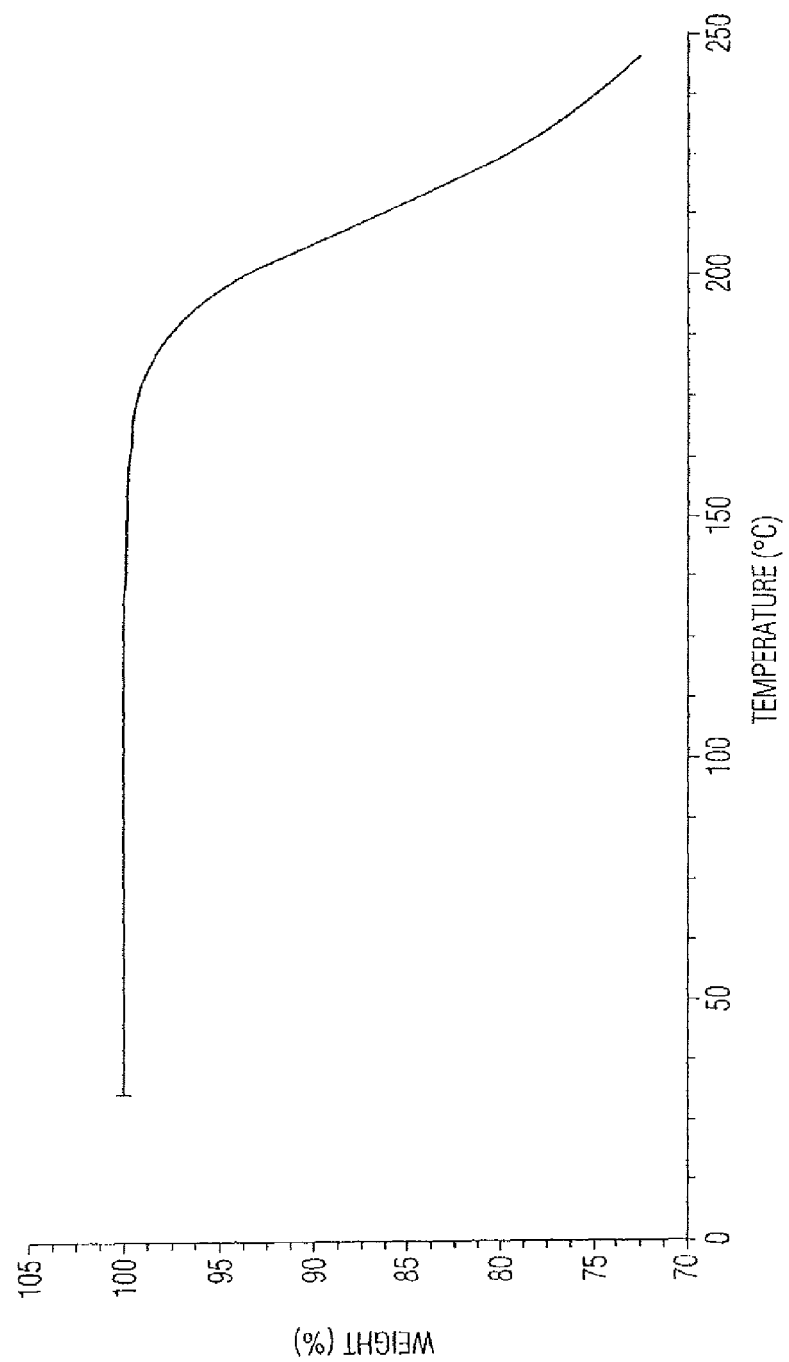
FIG. 27 is an illustration of TGA curve of crystalline sitagliptin mendelate prepared according to example 21.

For example, there is provided crystalline sitagliptin fumarate having PXRD characteristic peaks at approximately 6.19, 7.09, 15.93, 16.87, 17.12, 19.09, 21.87, 24.15, 25.26, 26.00 and 26.19±0.2 degrees 2 theta. The crystalline sitagliptin fumarate may be characterized by an PXRD pattern substantially as shown in FIG. 25. Crystalline sitagliptin fumarate may also be characterized by a DSC endotherm peak at about 187° C. The crystalline sitagliptin fumarate may be characterized by a DSC thermogram substantially as shown in FIG. 26. The crystalline sitagliptin fumarate may also be characterized by a TGA weight loss of about 0.238%. The crystalline sitagliptin fumarate may be characterized by a TGA curve substantially as shown by FIG. 27.

Figure 28:
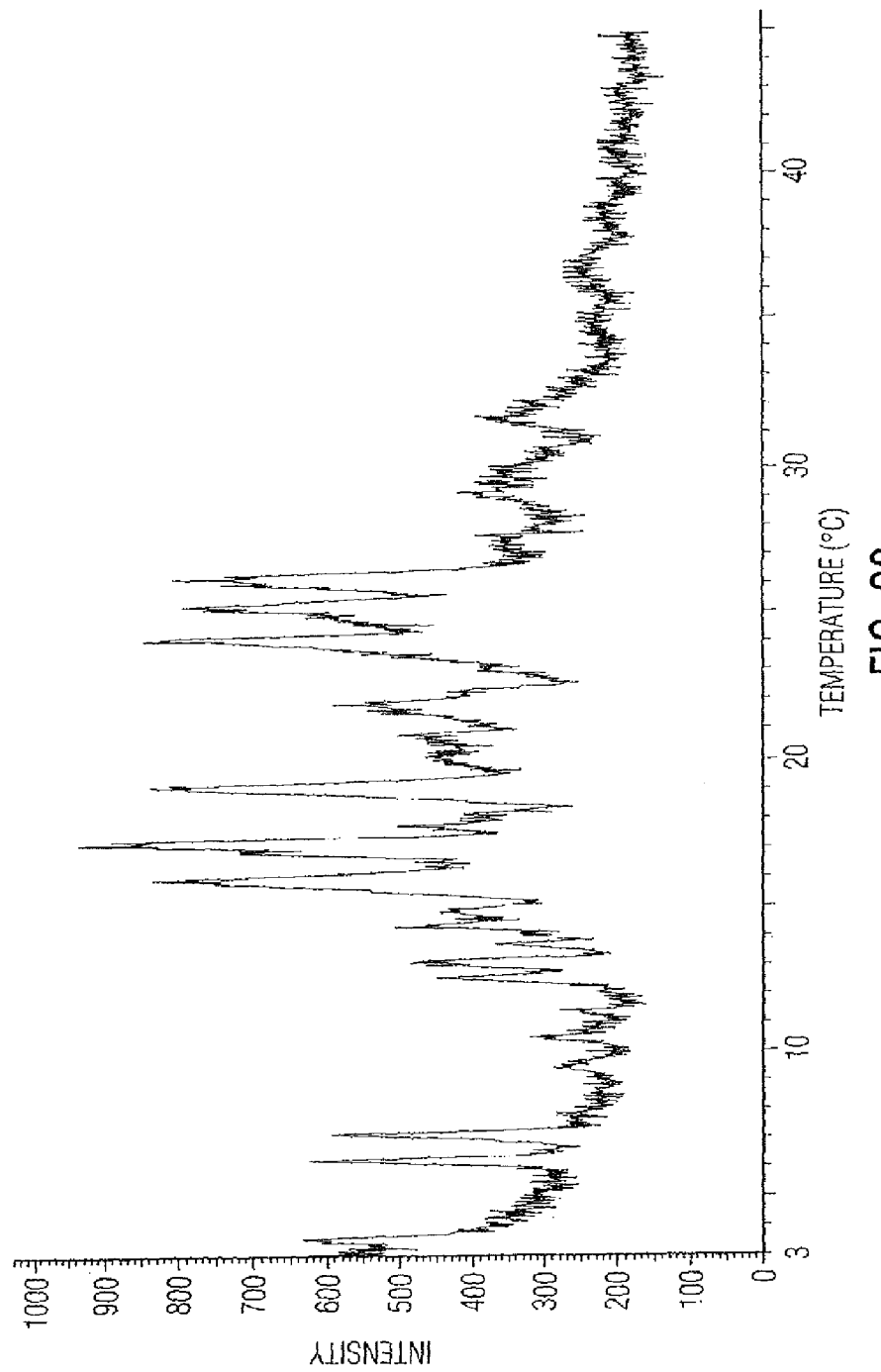
FIG. 28 is an illustration of PXRD pattern of crystalline sitagliptin fumarate prepared according to example 22.
Figure 29:
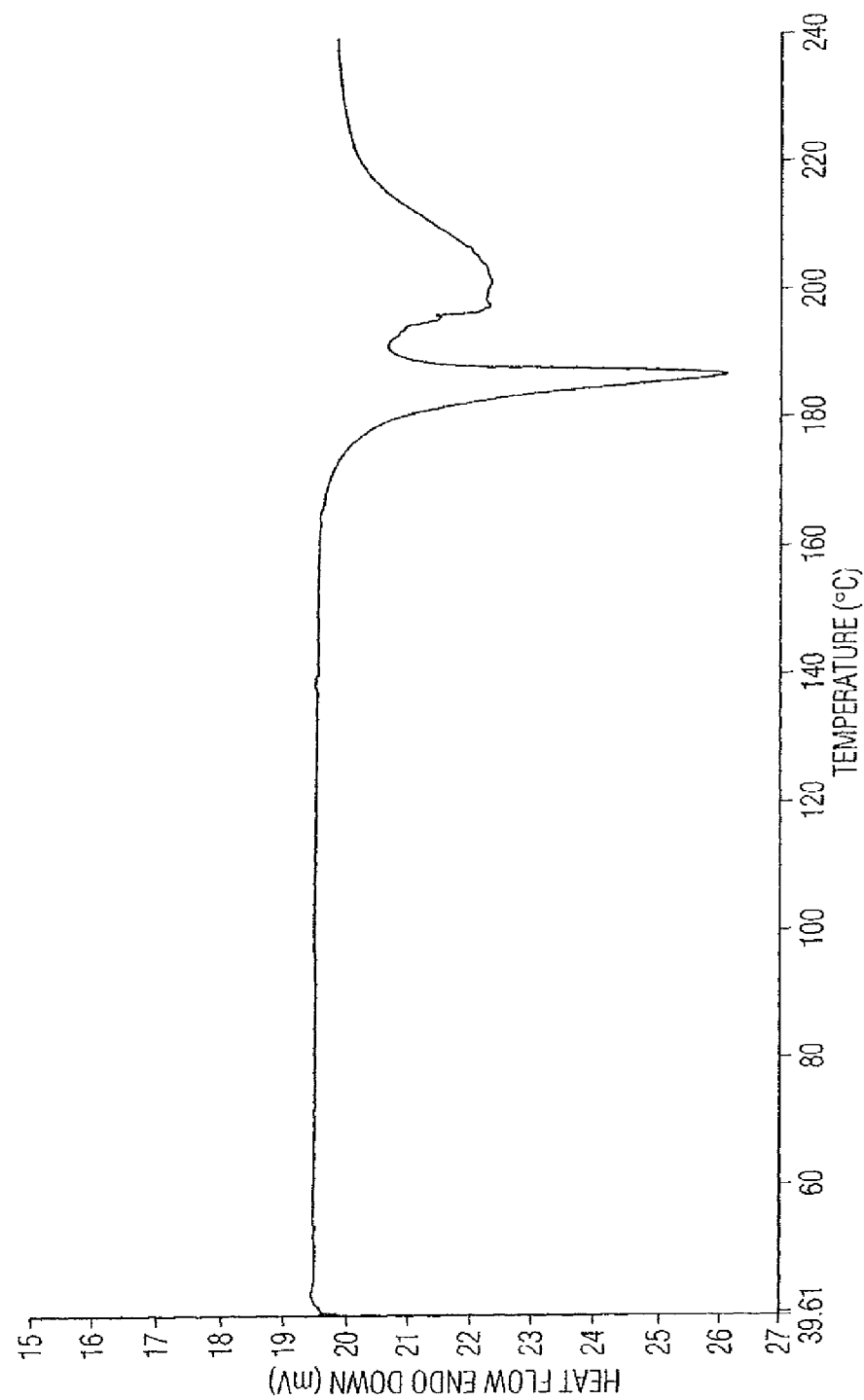
FIG. 29 is an illustration of DSC curve of crystalline sitagliptin fumarate prepared according to example 22.
Figure 30:
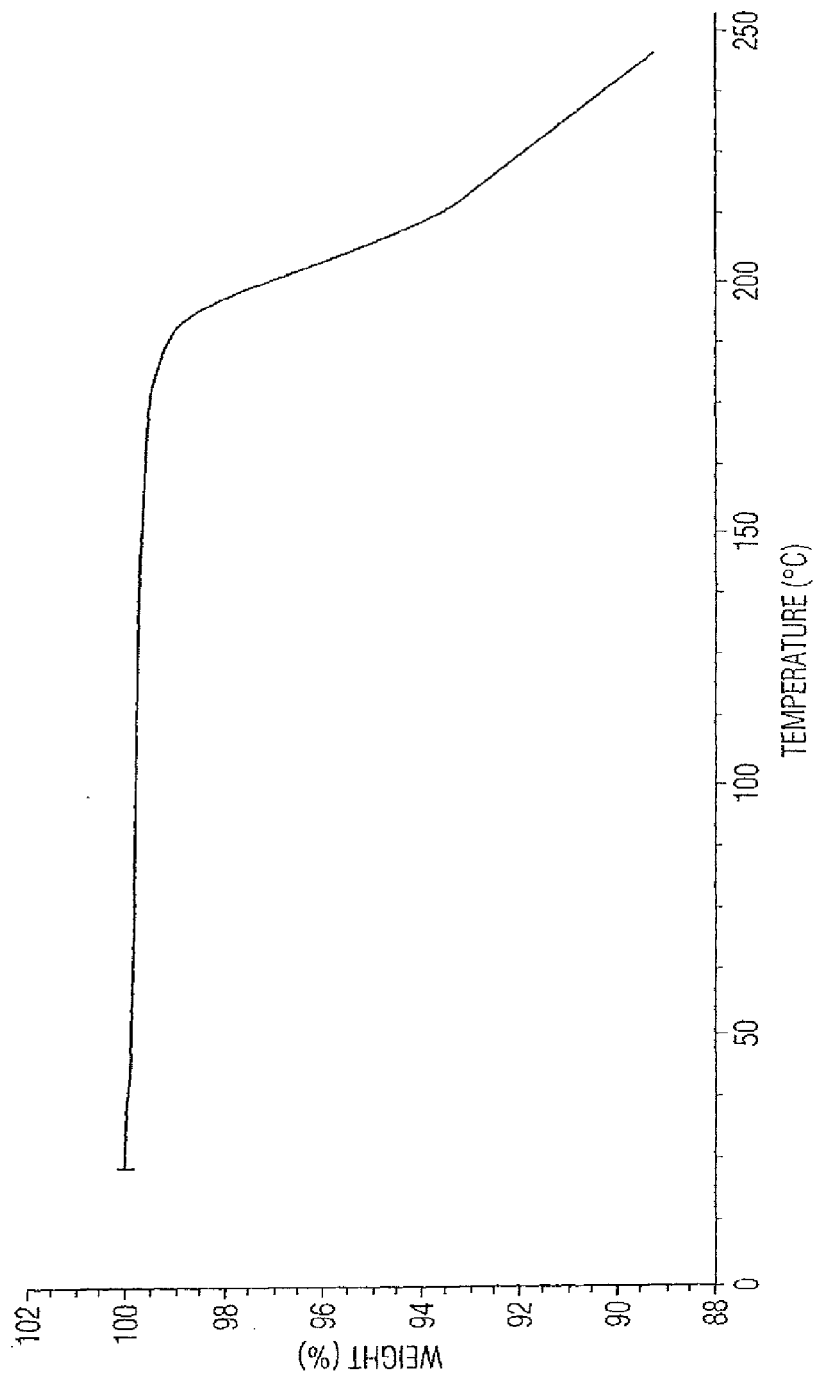
FIG. 30 is an illustration of TGA curve of crystalline sitagliptin fumarate prepared according to example 22.
Figure 31:
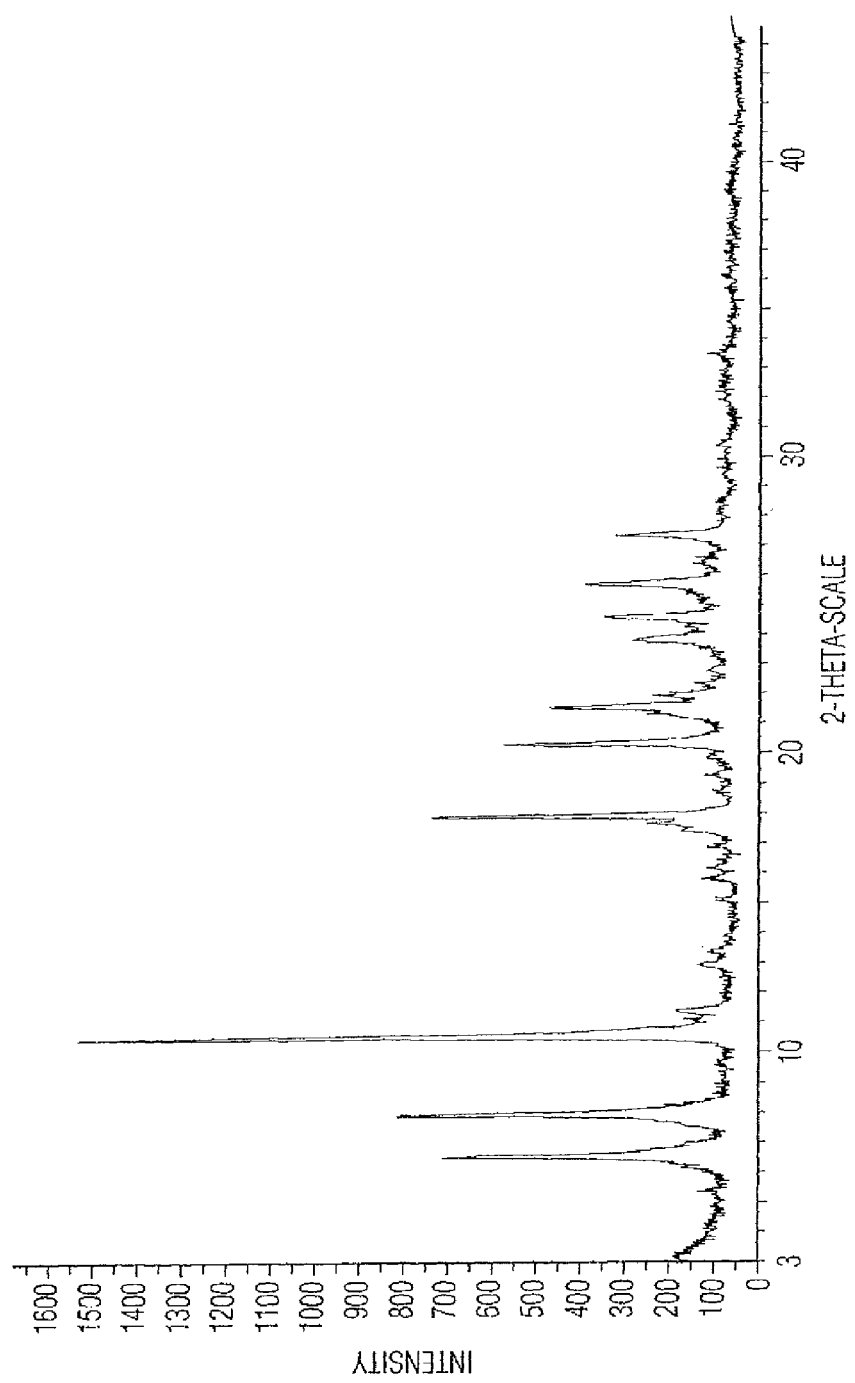
FIG. 31 is an illustration of PXRD pattern of crystalline sitagliptin lactate prepared according to example 23.
Figure 32:
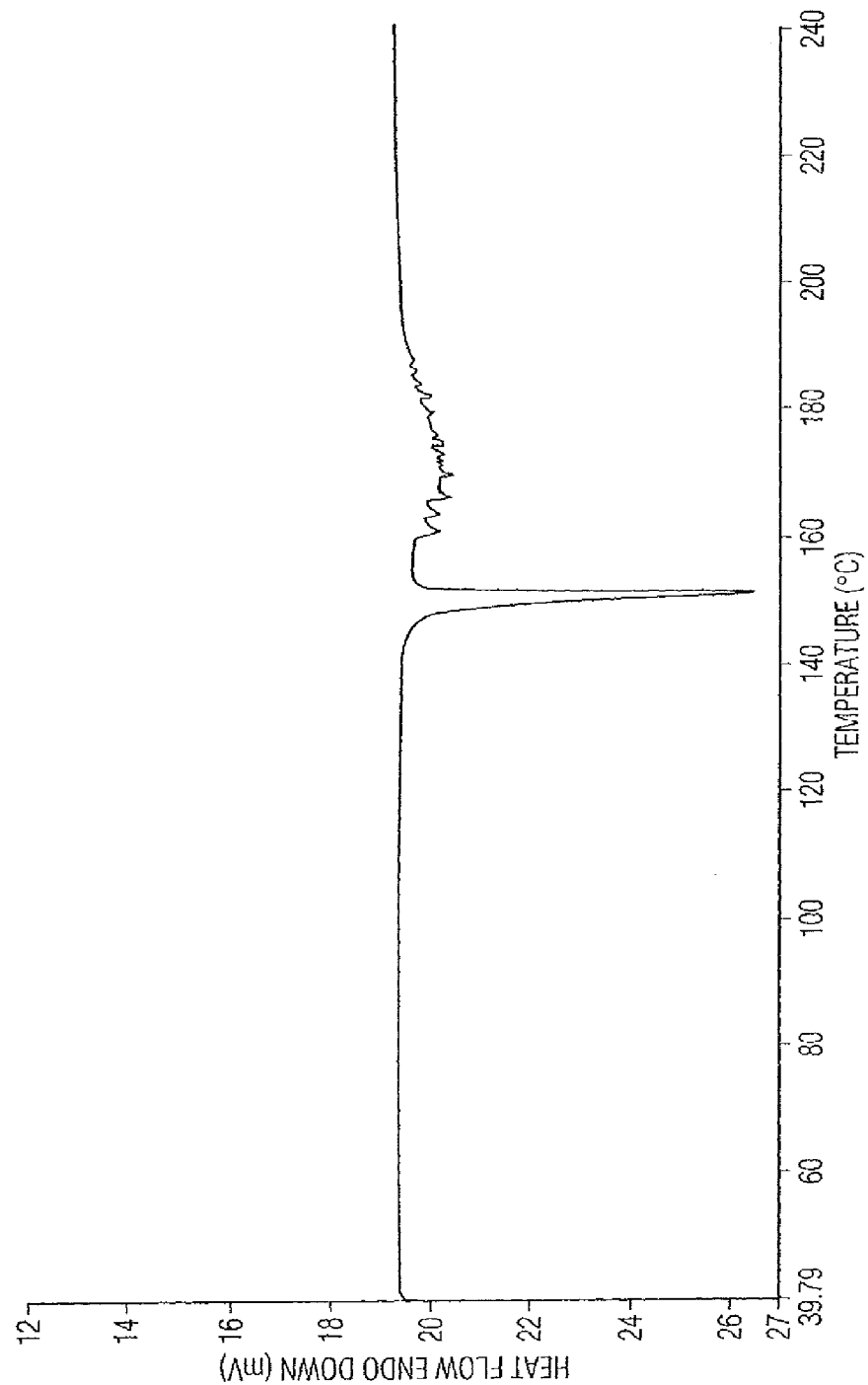
FIG. 32 is an illustration of DSC curve of crystalline sitagliptin lactate prepared according to example 23.
Figure 33:
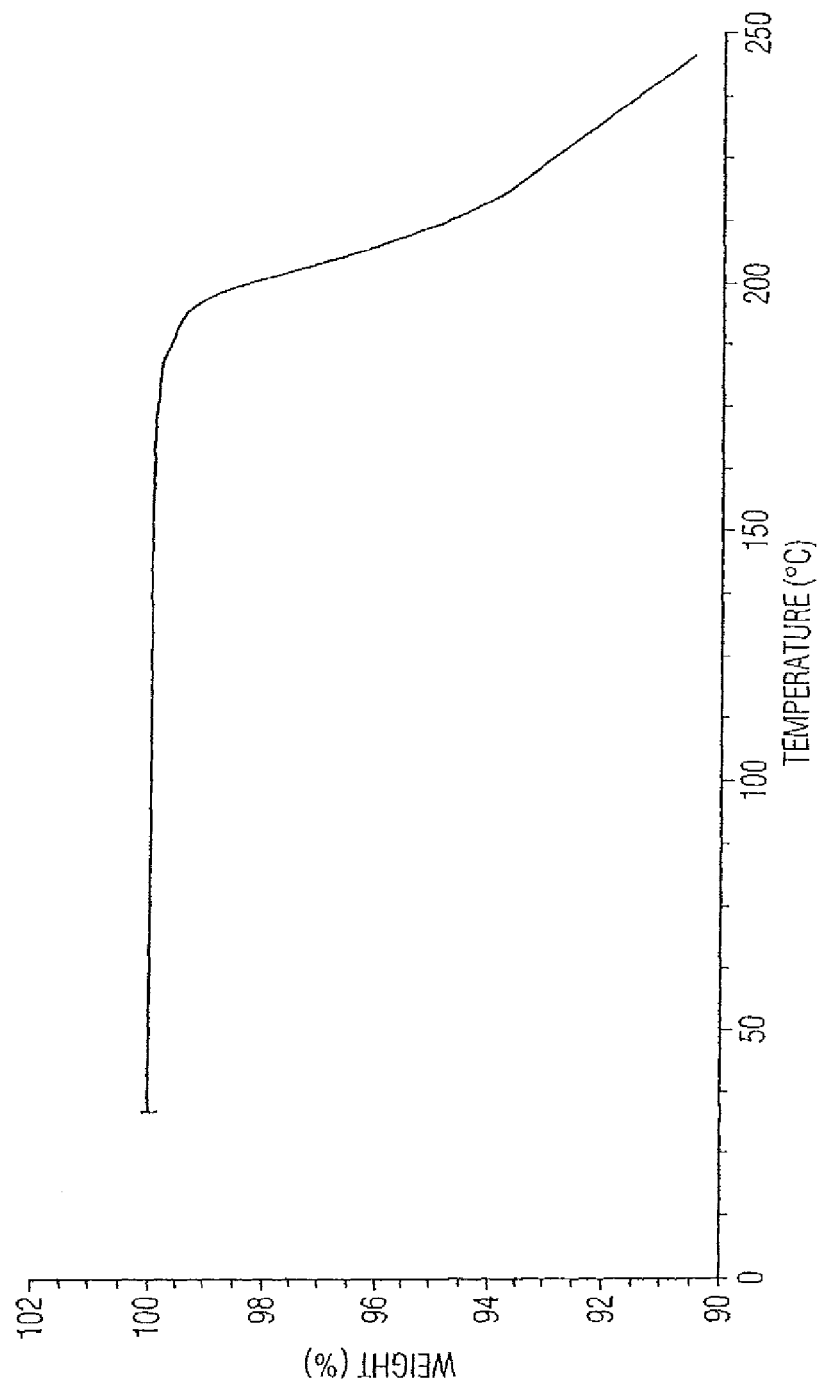
FIG. 33 is an illustration of TGA curve of crystalline sitagliptin lactate prepared according to example 23.

For example, there is provided crystalline sitagliptin lactate having PXRD characteristic peaks at approximately 7.91, 10.52, 17.66, 17.92, 20.34, 21.59, 23.87, 24.62 and 25.75±0.2 degrees 2 theta. The crystalline sitagliptin lactate may be characterized by an PXRD pattern substantially as shown in FIG. 28. Crystalline sitagliptin lactate may also be characterized by a DSC endotherm peak at about 151° C. The crystalline sitagliptin lactate may be characterized by a DSC thermogram substantially as shown in FIG. 29. The crystalline sitagliptin lactate may also be characterized by a TGA weight loss of about 0.06007%. The crystalline sitagliptin lactate may be characterized by a TGA curve substantially as shown by FIG. 30.

The present invention includes processes for the preparation of salts of sitagliptin, which processes comprise at least one of the steps of:

(a) providing a solution of a salt of sitagliptin in a solvent;

(b) isolating the salt of sitagliptin from the solution of Step (a); and (c) recovering the crystalline salt of sitagliptin and optionally drying it.

Step (a) involves providing a solution of a salt of sitagliptin in a solvent

The solution of a salt of sitagliptin may be obtained, for example, by dissolving a salt of sitagliptin of any form in a solvent. It may also be obtained by treating a reaction mixture comprising sitagliptin free base with an acid in a solvent, wherein the acid is sulfuric acid, hydrobromic acid, methanesulfonic acid, acetic acid, benzoic acid, oxalic acid, succinic acid, mandelic acid, fumaric acid lactic acid, or a combination thereof.

Solvents that may be used as in Step (a) include and are not limited to alcohols, such as, for example, methanol, ethanol, isopropanol, and n-butanol; organic acids, such as, for example, acetic acid and propionic acid; ketones, such as, for example, acetone, methyl isobutyl ketone, methyl ethyl ketone, and n-butanone; halogenated solvents, such as, for example, dichloromethane, ethylene dichloride, and chloroform; esters, such as, for example, ethyl acetate, n-propyl acetate, and isopropyl acetate; hydrocarbon solvents, such as, for example, toluene, xylene, n-hexane, n-heptane, and cyclohexane; ethers, such as, for example, 1,4-dioxane and tetrahydrofuran; aprotic polar solvents, such as, for example, N,N-dimethylformamide (DMF), dimethylsulfoxide (DMSO), and dimethylacetamide (DMA); or mixtures thereof.

If Step (a) involves dissolution of a salt of sitagliptin, the dissolution temperature may be less than about 100° C., or less than about 90° C., or less than about 80° C., or less than about 60° C., or less than about 50° C., or any other temperature, as long as the stability of the compound is not compromised and a clear solution is obtained.

In the case of salt formation in situ, suitable reaction mass temperature for addition of acid may be less than about 100° C., or less than about 90° C., or less than about 80° C., or less than about 60° C., or less than about 50° C., or any other temperature, as long as the stability of the compound is not compromised and a clear solution is obtained.

Step (b) involves isolating the salt of sitagliptin from the solution of Step (a).

The salt of sitagliptin may be isolated from the solution of the salt of sitagliptin by processes known in the art. Various isolation techniques that may be used for recovering the salt of sitagliptin include and not limited to precipitation by cooling, concentration, seeding, and adding anti-solvent; distillation; and evaporation. If desired, the solution may be concentrated by conventional methods such as evaporation, distillation before cooling the solution. The exact cooling temperature and time required for complete crystallization may be readily determined by a person skilled in the art and will also depend on parameters, such as concentration and temperature of the solution or slurry. Stirring or other methods, such as shaking, agitation, and the like, that mix the contents thoroughly may be employed for crystallization to occur.

During isolation of the crystals, the suspension may be maintained for a time sufficient to achieve the complete isolation of the product with desired yield and quality. Such a time may vary from about 1 to about 48 hours or longer.

Step (c) involves recovering the crystalline salt of sitagliptin and optionally drying it The crystalline solid may then be recovered from the suspension by using any of techniques, such as filtration by gravity or by suction, centrifugation, slow evaporation, or any other suitable technique. The crystals so isolated may carry a small proportion of occluded mother liquor containing a higher percentage of impurities. If desired, the crystals may be washed with a solvent to wash out the mother liquor and/or impurities, and the resulting wet crystals may optionally be suction dried.

The wet cake obtained in Step (c) may be optionally dried. Drying may be carried out in a tray dryer, vacuum oven, air oven, fluidized bed drier, spin flash dryer, flash dryer, and the like. The drying may be carried out at temperature of less than about 200° C., between about 20° C. to about 80° C., between about 30° C. to about 60° C., or any other suitable temperature, at atmospheric pressure or under reduced pressure. The drying may be carried out for any desired time until the desired quality of product is achieved.

The present invention includes pharmaceutical compositions containing a therapeutically effective amount of sitagliptin or a pharmaceutically acceptable salt thereof, containing less than about 0.1% of any individual impurity, together with one or more pharmaceutically acceptable excipients.

Pharmaceutical compositions according to the present invention may be formulated as: solid oral dosage forms including powders, granules, pellets, tablets, and capsules; liquid oral dosage forms including syrups, suspensions, dispersions, and emulsions; and injectable preparations including solutions, dispersions, and freeze dried compositions. Formulations may be adapted for immediate release, delayed release, or modified release of the active ingredient. Immediate release compositions may be conventional, dispersible, chewable, mouth dissolving, or flash melt preparations. Modified release compositions may comprise hydrophilic and/or hydrophobic, release rate controlling substances to form matrix and/or reservoir systems. The pharmaceutical compositions may be prepared by direct blending, dry granulation, wet granulation, extrusion, and/or spheronization. The pharmaceutical compositions may be presented as uncoated, film coated, sugar coated, powder coated, enteric coated, or modified release coated.

Compositions of the present invention comprise one or more pharmaceutically acceptable excipients. Pharmaceutically acceptable excipients that find use in the present invention include and are not limited to: diluents, such as, for example, starch, pregelatinized starch, lactose, powdered cellulose, microcrystalline cellulose, dicalcium phosphate, tricalcium phosphate, mannitol, sorbitol, sugar, and the like; binders, such as, for example, acacia, guar gum, tragacanth, gelatin, polyvinylpyrrolidone, hydroxypropyl cellulose, hydroxypropyl methylcellulose, pregelatinized starch, and the like; disintegrants, such as, for example, starch, sodium starch glycolate, pregelatinized starch, crospovidone, croscarmellose sodium, colloidal silicon dioxide, and the like; lubricants, such as, for example, stearic acid, magnesium stearate, zinc stearate, and the like; glidants, such as, for example, colloidal silicon dioxide and the like; solubility or wetting enhancers, such as, for example, anionic, cationic, or neutral surfactants; complex forming agents, such as, for example, various grades of cyclodextrins and resins; release rate controlling agents, such as, for example, hydroxypropyl cellulose, hydroxymethyl cellulose, hydroxypropyl methylcellulose, ethyl cellulose, methylcellulose, various grades of methyl methacrylates, waxes, and the like. Other pharmaceutically acceptable excipients that are of use include but are not limited to film formers, plasticizers, colorants, flavoring agents, sweeteners, viscosity enhancers, preservatives, antioxidants, and the like.

Certain specific aspects and embodiments of the present application will be explained in greater detail with reference to the following examples, which are provided by way of illustration only and should not be construed as limiting the scope of the application in any manner.

PXRD data reported herein was obtained using Cu Ka radiation, having the wavelength 1.5418 Å and were obtained using a Bruker AXS D8 Advance Powder X-ray Diffractometer.

DSC analysis was carried out in a DSC Q1000 instrument from TA Instruments with a ramp of 10° C./minute with a

EXAMPLES

Reference Example

Preparation of 3-trifluoromethyl-5,6,7,8-tetrahydro-1,2,4-triazolo[4,3-a]pyrazine hydrochloride of Formula X Step A: Preparation of N'-(2-chloroacetyl)-trifluoroacetohydrazide Hydrazine hydrate (15 g, 35 wt %) is mixed acetonitrile (22.5 mL) and cooled to about 10° C. Ethyl trifluoroacetate (23.3 g) is added over 1 hour. The resulting solution is warmed to 20° C. and stirred for about 1 hour. The solution is cooled to 0-2° C. 50 wt % aqueous NaOH (7.88 g) and chloroacetyl chloride (22.2 g) are added to the reaction solution simultaneously over 2 hours. The reaction mixture is warmed to 15-18° C. and stirred for about 5 hours. Solvent is distilled off under vacuum at about 30° C. Water (50 mL) and ethyl acetate (100 mL) are added to the obtained crude. The organic and aqueous layers are separated and aqueous layer is washed with ethyl acetate (2×50 mL). The organic layers are combined and washed with water (2×50 mL) followed by washing with 15% sodium chloride solution (2×50 mL). The combined organic layer is dried over sodium sulfate. The solvent is completely distilled off under vacuum to afford the title compound. (Yield: 98.3%)

Step B: Preparation of 5-trifluoromethyl-2-chloromethyl-1,3,4-oxadiazole

N'-(2-chloroacetyl)-trifluoroacetohydrazide (60 g) and acetonitrile (120 mL) are charged into a round-bottom flask and cooled to about 0° C. Phosphorus oxychloride (27.1 g) is added to the solution for about 15 minutes. The reaction mixture is heated to about 80° C. and stirred for about 28 hours. In a separate vessel, isopropyl acetate (180 mL) and water (180 mL) are mixed and cooled to 0° C. The reaction slurry is added to this solution slowly. The organic layer is separated and washed with 5% sodium bicarbonate solution (180 mL) and finally with 20% sodium chloride solution (180 mL). The organic layer is dried over sodium sulfate. The solvent is completely distilled off under vacuum to afford the title compound. (Yield: 82.2%)

Step C: Preparation of N'-((Z)-piperazin-2-ylidene)-trifluoroacetohydrazide

The solution of ethylene diamine (89 g) in methanol (305 mL) is stirred and cooled to −20° C. over about 45 minutes. 5-(trifluoromethyl)-2-(chloromethyl)-1,3,4-oxadiazole (79 g) is added slowly to the solution over 90 minutes at −20° C. The resulting slurry is stirred for about 90 minutes at −20° C. Ethanol (482 mL) is added and the slurry is warmed to −5° C. After stirring for about 2 hours at −5° C., the solid is filtered, washed with ethanol (79 mL) and dried at about 55° C. to afford the title compound. (Yield: 46.8%)

Step D: Preparation of 3-trifluoromethyl-5,6,7,8-tetrahydro-1,2,4-triazolo[4,3-a]pyrazine hydrochloride (Formula X)

A suspension of N'-((Z)-piperazin-2-ylidene)-trifluoroacetohydrazide (41 g) in methanol (170 mL) is stirred and heated to about 55° C. Hydrogen chloride (21 mL) is added to the reaction mixture and stirred for about 2 hours. The solution is cooled to 20° C. and methyl tert-butyl ether (423 mL) is added to it. The solution is further cooled to 0° C. and stirred for about 1 hour. The solid is filtered, washed with mixture of ethanol and methyl tert-butyl ether (82 mL) and dried at about 45° C. to afford the title compound. (Yield: 90.7%)

Example 1

Preparation of 5-(1-hydroxy-2-(2,4,5-trifluorophenyl)-ethylidene)-2,2-dimethyl-1,3-dioxane-4,6-dione (Formula XI)

2,4,5-trifluorophenylacetic acid (30 g), tetrahydrofuran (360 mL), 1,1-carbonyl diimidazole (25.5 g) at about 50° C., and meldrums acid (22.7 g) are combined. The mixture is stirred for about five hours at the same temperature. The reaction mass is then cooled to about 30° C. Isopropyl acetate (180 mL) and water (180 mL) are added and stirred for about 30 minutes. The reaction mass is cooled to about 0° C. and pH is adjusted to about 2.4 using 36% aqueous hydrochloric acid. The organic layer is separated, washed with 0.1 N aqueous hydrochloric acid and distilled off completely. To the residue obtained, n-heptane (140 mL) and isopropyl acetate (70 mL) are charged at about 30° C. and stirred at about 0° C. for about 90 minutes. The separated solid is filtered and washed with a mixture of n-heptane (20 mL) and isopropyl acetate (10 mL). The wet cake is dried at about 50° C. for about 4 hours to afford the title compound. (Yield: 60.1%; purity by HPLC: 98.0%)

Example 2

Preparation of 7-(1,3-dioxo-4-(2,4,5-trifluorophenyl)-butyl)-3-trifluoromethyl-5,6,7,8-tetrahydro-1,2,4-triazolo[4,3-a]pyrazine (Formula VI)

A mixture of 5-(1-hydroxy-2-(2,4,5-trifluorophenyl)-ethylidene)-2,2-dimethyl-1,3-dioxane-4,6-dione (10 g), 3-trifluoromethyl-5,6,7,8-tetrahydro-1,2,4-triazolo[4,3-a]pyrazine hydrochloride (7.2 g), diisopropyl ethylamine (4.5 g), and isopropyl acetate (100 mL) are heated to about 85° C. and stirred for about 4 hours. The reaction mass is then cooled to about 30° C. and quenched with water (90 mL). The organic layer is separated, washed with 5% sodium chloride solution (3×50 mL) and distilled off completely under vacuum to afford 12 g of the title compound. (Yield: 93.3%; purity by HPLC: 95.7%)

Example 3

Preparation of 7-(1-oxo-3-amino-4-(2,4,5-trifluorophenyl)-but-2-enyl)-3-trifluoromethyl-5,6,7,8-tetrahydro-1,2,4-triazolo[4,3-a]pyrazine (Formula V)

A mixture of 7-(1,3-dioxo-4-(2,4,5-trifluorophenyl)-butyl)-3-trifluoromethyl-5,6,7,8-tetrahydro-1,2,4-triazolo[4,3-a]pyrazine (22.1 g), ammonium acetate (25 g), methanol (220 mL), and aqueous ammonia (22 mL) are heated to about 55° C. and stirred for about 6 hours. The reaction mass is then cooled to 30° C. and the undissolved particles are filtered off. The filtrate is distilled off completely under vacuum. To the residue, ethanol (25 mL) is charged and the mixture is stirred at about 30° C. for about 30 minutes. The solid is filtered, washed with ethanol (5 mL), and dried to afford the title compound. (Yield: 75%; purity by HPLC: 96.7%)

Example 4

Preparation of 7-(1-oxo-3-amino-4-(2,4,5-trifluorophenyl)-butyl)-3-(trifluoromethyl)-5,6,7,8-tetrahydro-1,2,4-triazolo[4,3-a]pyrazine (Formula IV)

A mixture of methanol (135 ml), 7-(1-oxo-3-amino-4-(2,4,5-trifluorophenyl)-but-2-enyl)-3-trifluoromethyl-5,6,7,8-tetrahydro-1,2,4-triazolo[4,3-a]pyrazine (13.5 gm), sodium cyano borohydride (2.5 g), and methanolic hydrogen chloride (35 mL) at about 4.5 pH is stirred for about 5 hours at about 30° C. The solvent is distilled off completely and water (50 mL) is added to the residue. The extraction is carried out with ethylacetate (150 mL). The obtained organic layer is distilled off completely to afford the title compound. (Yield: 99.9%; purity by HPLC: 92.25%)

Example 5

Preparation of Sitagliptin di-p-tolyl-L-tartarate salt

A mixture of methanol (390 mL), water (80 mL), 7-(1-oxo-3-amino-4-(2,4,5-trifluorophenyl)-butyl)-3-trifluoromethyl-5,6,7,8-tetrahydro-1,2,4-triazolo[4,3-a]pyrazine (13 g), and di-p-tolyl-L-tartaric acid (13 g) is stirred for about 24 hours. The separated solid is filtered off, washed with ethanol (15 mL) and dried at about 45° C. to afford the title compound. (Yield: 66.3%; purity by HPLC: 99.93%)

Example 6

Preparation of Sitagliptin phosphate monohydrate (Formula I)

10% sodium hydroxide solution (1 mL) is added to a mixture of ethylacetate (10 mL), water (5 mL), sitagliptin di-p-tolyl-L-tartarate (0.4 g) under stirring at about 5° C. The mixture is stirred for about 30 minutes. The layers are separated and the aqueous layer is extracted with ethyl acetate (10 mL). The combined organic layer is distilled off completely to afford 0.2 gm of sitagliptin freebase.

The sitagliptin freebase is dissolved in a mixture of isopropyl alcohol (5 mL) and water (0.2 mL), to which 85% phosphoric acid (0.056 g) is added. The contents are heated to about 70° C. for about 30 minutes, then cooled to about 30° C., and stirred for about 15 hours. The separated solid is filtered, washed with isopropyl alcohol (1 mL), and dried at about 50° C. for about 3 hours to afford the title compound. (Yield: 68%; purity by HPLC: 99.87%; SOR: −20.7° C. (c=1% in water))

Example 7

Preparation of (Z)-7-(1-oxo-3((R)-1-phenylethylamino)-4-(2,4,5-trifluorophenyl)-but-2-enyl)-3-trifluoromethyl-5,6,7,8-tetrahydro-1,2,4-triazolo[4,3-a]pyrazine (Formula VIII)

A mixture of isopropanol (10 mL), 7-(1,3-dioxo-4-(2,4,5-trifluorophenyl)-butyl)-3-trifluoromethyl-5,6,7,8-tetrahydro-1,2,4-triazolo[4,3-a]pyrazine (2 g), and R-1-phenylethanamine are heated to about 40° C. Acetic acid (0.15 mL) is added and stirred for about 5 hours. The solvent is distilled off completely to afford the title compound. (Yield: 99.7%; m/z: 510 (m+1))

Example 8

Preparation of 7-(1-oxo-3((R)-((R)-1-phenylethylamino))-4-(2,4,5-trifluorophenyl)-butyl)-3-trifluoromethyl-5,6,7,8-tetrahydro-1,2,4-triazolo[4,3-a] pyrazine (Formula IX)

Tetrahydrofuran (80 ml), methanol (20 ml), (Z)-7-(1-oxo-3((R)-1-phenylethylamino)-4-(2,4,5-trifluorophenyl)-but-2-enyl)-3-trifluoromethyl-5,6,7,8-tetrahydro-1,2,4-triazolo[4,3-a]pyrazine (8 g), and platinum oxide (1.0 g) are charged in an autoclave vessel and the contents are heated to about 40° C. $H_2$ gas pressure of about 12-14 kg/cm$^2$ is applied and maintained for about 10 hours at the same temperature. The reaction mass is then cooled to about 30° C. and then the catalyst is filtered off. The filtrate is distilled off completely under vacuum to afford 8.2 gm of the title compound.

Example 9

Preparation of Sitagliptin (Formula II)

Tetrahydrofuran (10 mL), methanol (10 mL), 7-(1-oxo-3 ((R)-((R)-1-phenylethylamino))-4-(2,4,5-trifluorophenyl)-butyl)-3-trifluoromethyl-5,6,7,8-tetrahydro-1,2,4-triazolo[4,3-a]pyrazine (2 g), formic acid (2 mL), 20% palladium hydroxide carbon (0.5 g), and water (2 mL) are charged in a round-bottom flask and the contents are heated to about 60° C. for about 6 hours. The reaction mass is then cooled to about 30° C. and the catalyst is filtered. The filtrate is distilled off completely under vacuum. Water (10 mL) and ethyl acetate (20 mL) are charged to the residue and it is cooled to about 0° C. Phosphoric acid (0.4 g) is added to the reaction mass and the layers are separated. Aqueous layer is cooled to about 0° C. and 5% sodium hydroxide is added till pH of the mass is attained to about 12.0. The mass is then extracted with ethyl acetate (20 mL) and the ethyl acetate layer is distilled off completely to afford the title compound. (Yield: 79.4%)

Example 10

Preparation of Sitagliptin phosphate monohydrate (Formula I)

7-[(3R)-3-Amino-1-oxo-4-(2,4,5-trifluorophenyl)butyl]-5,6,7,8-tetrahydro-3-(trifluoromethyl)-1,2,4-triazolo[4,3-a]pyrazine of Formula II (0.4 g), isopropanol (5 mL), water (0.4 mL), and phosphoric acid (0.11 g) are charged and heated to about 70° C. for about 3 hours. The reaction mass is then cooled to about 30° C. and stirred for about 10 hours. The separated solid is filtered and dried at about 45° C. under vacuum for about 4 hours to afford the title compound. (Yield: 68%; purity by HPLC: 96.67%; purity by chiral HPLC: 99.19%; m/z: 408(m+1); SOR: −21° C. (c=1% in water))

Example 11

Preparation of Sitagliptin (Formula II)

10% sodium hydroxide solution (10 mL) is added to a mixture of 7-(1-oxo-3-((R)-amino)-4-(2,4,5-trifluorophenyl)-butyl)-3-trifluoromethyl-5,6,7,8-tetrahydro-1,2,4-triazolo[4,3-a]pyrazine di-p-tolyl-L-tartarate salt (8.5 g), and ethyl acetate (30 mL) at about 10° C. The mixture is stirred at the same temperature until clear. The layers are then separated and the organic layer is distilled completely. Isopropanol (5 mL) is charged and stirred until the solution is clear. To the solution, n-heptane (25 mL) is charged and stirred for about 9 hours. The solid is filtered, washed with n-heptane (5 mL), and dried under reduced pressure to afford the title compound. (Yield: 99.5%)

Example 12

Preparation of Sitagliptin phosphate monohydrate (Formula I)

A mixture of 7-(1-oxo-3-((R)-amino-4-(2,4,5-trifluorophenyl)-butyl)-3-trifluoromethyl-5,6,7,8-tetrahydro-1,2,4-triazolo[4,3-a]pyrazine (2 gm), water (2 mL), isopropanol (4 mL), and 85% phosphoric acid (0.567 g) is heated to about 75° C. and stirred until the mixture is clear. The mixture is then cooled to about 68° C. and stirred for about 2 hours. It is further cooled to about 4° C. and stirred overnight. Isopropanol (14 mL) is charged and stirred for about one hour. The solid is filtered and washed with mixture of isopropanol (4.5 mL) and water (0.5 mL) to afford the title compound. (Yield: 93.38%; purity by HPLC: 99.96%)

Example 13

Preparation of Anhydrous Crystalline Sitagliptin Dihydrogen Phosphate (Form A)

10% sodium hydroxide solution (15 mL) is added to a mixture of ethyl acetate (25 mL), water (20 mL), and sitagliptin di-p-tolyl-tartarate salt (8.0 g) under stirring at about 5° C. The mixture is stirred for about 30 minutes. The layers are separated and the aqueous layer is extracted with ethyl acetate (50 mL). The combined organic layer is distilled off completely to afford 4.1 g of sitagliptin freebase.

The sitagliptin freebase is dissolved in a mixture of isopropanol (80 mL) and water (4.0 mL). 85% phosphoric acid (1.13 g) is added. The contents are heated to about 70° C. for about 30 minutes, then cooled to about 30° C., and stirred for about 15 hours. The separated solid is filtered, washed with isopropanol (1 mL), and dried at about 50° C. for about 3 hours to afford the title compound. (Yield: 85.6%; purity by HPLC: 99.96%)

Example 14

Preparation of Sitagliptin Sulfate

Sitagliptin (5 g) and isopropanol (75 mL) are charged into a round-bottom flask and the mixture is heated to about 80° C. for about 15 minutes to obtain a clear dissolution. Sulfuric acid (1.2 g) is added and the reaction mixture is refluxed for about 1 hour. The reaction mixture is cooled to about 30° C. and stirred for about 22 hours. The separated solid is filtered, washed with isopropanol (5 mL), and dried under reduced pressure at about 40° C. for about 1.5 hours to afford the title compound. (Yield: 6.0 g; MC: 0.84% w/w; HPLC purity: 99.98%)

Example 15

Preparation of Sitagliptin Hydrobromide

Sitagliptin (5 g) and isopropanol (75 mL) are charged into a round-bottom flask and the mixture is heated to about 80° C. for about 30 minutes to obtain a clear dissolution. Hydrobromic acid (2.1 g) is added and the reaction mixture is refluxed for about 1.5 hours. The reaction mixture is cooled to about 30° C. and stirred for about 22 hours. The separated solid is filtered, washed with isopropanol (5 mL), and dried under reduced pressure at about 35° C. for about 1.25 hours to afford the title compound. (Yield: 4.0 g; MC: 2.40% w/w; HPLC purity: 99.70%)

Example 16

Preparation of Sitagliptin Methane Sulfonate

Sitagliptin (5 g) and isopropanol (50 mL) are charged into a round-bottom flask and the mixture is heated to about 80° C. for about 20 minutes to obtain a clear dissolution. Methane sulfonic acid (1.11 g) is added and the reaction mixture is refluxed for about 1.5 hours. The reaction mixture is cooled to about 30° C. and stirred for about 16 hours. The separated solid is filtered, washed with isopropanol (5 mL), and dried under reduced pressure at about 45° C. for about 2.5 hours to afford the title compound. (Yield: 6.0 g; MC: 0.97% w/w; HPLC purity: 99.92%)

Example 17

Preparation of Sitagliptin Acetate

Sitagliptin (5 g) and isopropanol (75 mL) are charged into a round-bottom flask and the mixture is heated to about 80° C. for about 20 minutes to obtain a clear dissolution. Acetic acid (0.73 g) is added and the reaction mixture is refluxed for about 1.5 hours. The reaction mixture is cooled to about 30° C. and stirred for about 8.5 hours. The separated solid is filtered, washed with isopropanol (5 mL), and dried under reduced pressure at about 30° C. for about 3.5 hours to afford the title compound. (Yield: 5.6 g; MC: 0.79% w/w; HPLC purity: 99.81%)

Example 18

Preparation of Sitagliptin Benzoate

Sitagliptin (5 g) and isopropanol (75 mL) are charged into a round-bottom flask and the mixture is heated to about 80° C. for about 20 minutes to obtain a clear dissolution. Benzoic acid (1.49 g) is added and the reaction mixture is refluxed for about 1.5 hours. The reaction mixture is cooled to about 30° C. and stirred for about 21.5 hours. The separated solid is filtered, washed with isopropanol (5 mL), and dried under reduced pressure at about 40° C. for about 1.5 hours to afford the title compound. (Yield: 5.9 g; MC: 0.80% w/w; HPLC purity: 99.82%)

Example 19

Preparation of Sitagliptin Oxalate

Sitagliptin (5 g) and isopropanol (75 mL) are charged into a round-bottom flask and the mixture is heated to about 80° C. for about 30 minutes to obtain a clear dissolution. Oxalic acid (1.54 g) dissolved in water (5 mL) is added and the reaction mixture is refluxed for about 1 hour. The reaction mixture is cooled to about 30° C. and stirred for about 22 hours. The separated solid is filtered, washed with isopropanol (5 mL), and dried under reduced pressure at about 40° C. for about 2.5 hours to afford the title compound. (Yield: 5.8 g; MC: 6.54% w/w; HPLC purity: 99.95%)

Example 20

Preparation of Sitagliptin Succinate

Sitagliptin (5 g) and isopropanol (50 mL) are charged into a round-bottom flask and the mixture is heated to about 80° C. for about 30 minutes to obtain a clear dissolution. Succinic acid (1.44 g) is added and the reaction mixture is refluxed for about 1.5 hours. The reaction mixture is cooled to about 30° C. and stirred for about 23 hours. The separated solid is filtered, washed with isopropanol (5 mL), and dried under reduced pressure at about 50° C. for about 3 hours to afford the title compound. (Yield: 4.0 g; MC: 1.79% w/w; HPLC purity: 99.72%)

Example 21

Preparation of Sitagliptin Mandelate

Sitagliptin (4 g) and isopropanol (60 mL) are charged into a round-bottom flask and the mixture is heated to about 80° C. for about 30 minutes to obtain a clear dissolution. Mandelic acid (1.49 g) is added and the reaction mixture is refluxed for about 1.5 hours. The reaction mixture is cooled to about 30° C. and stirred for about 21.5 hours. The separated solid is filtered, washed with isopropanol (4 mL), and dried under reduced pressure at about 45° C. for about 2 hours to afford the title compound. (Yield: 4.4 g; MC: 0.51% w/w; HPLC purity: 99.56%)

Example 22

Preparation of Sitagliptin Fumarate

Sitagliptin (4 g) and isopropanol (60 mL) are charged into a round-bottom flask and the mixture is heated to about 80° C. for about 30 minutes to obtain a clear dissolution. Fumaric acid (1.14 g) is added and the reaction mixture is refluxed for about 2 hours. The reaction mixture is cooled to about 30° C. and stirred for about 21 hours. The separated solid is filtered, washed with isopropanol (4 mL), and dried under reduced pressure at about 45° C. for about 2 hours to afford the title compound. (Yield: 4.0 g; MC: 1.05% w/w; HPLC purity: 99.47%)

Example 23

Preparation of Sitagliptin Lactate

Sitagliptin (5 g) and isopropanol (75 mL) are charged into a round-bottom flask and the mixture is heated to about 80° C. for about 20 minutes to obtain a clear dissolution. Lactic acid (1.10 g) is added and the reaction mixture is refluxed for about 1.5 hours. The reaction mixture is cooled to about 30° C. and stirred for about 8.5 hours. The separated solid is filtered, washed with isopropanol (5 mL), and dried under reduced pressure at about 45° C. for about 2 hours to afford the title compound. (Yield: 4.0 g; MC: 0.62% w/w; HPLC purity: 99.75%)

The invention claimed is:

1. A compound of Formula IX or a pharmaceutically acceptable salt thereof,

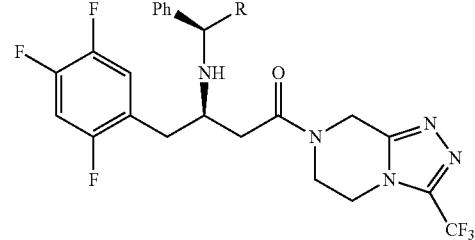

Formula IX wherein R is $C_1$-$C_4$ alkyl.

2. The compound of claim 1 which is,

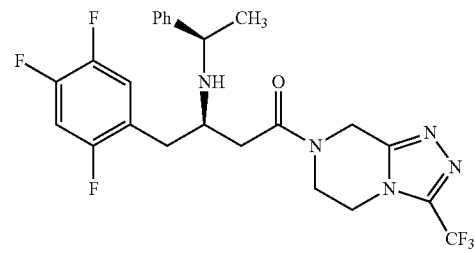 [SMILES: C[C@@H](N[C@@H](CC(=O)N1CCn2c(nnc2C(F)(F)F)C1)Cc1cc(F)c(F)cc1F)c1ccccc1]

or a pharmaceutically acceptable salt thereof.

3. A process for the preparation of sitagliptin of the formula II

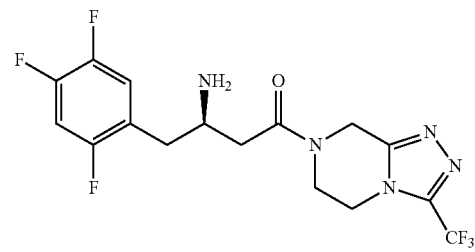

Formula II or a pharmaceutically acceptable salt thereof, comprising
   a) the deprotection of a compound of Formula IX or a pharmaceutically acceptable salt thereof,

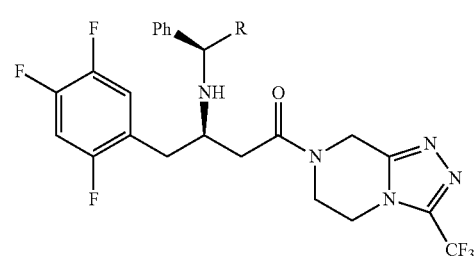

Formula IX wherein R is $C_1$-$C_4$ alkyl, and b) optionally, treating a compound of Formula II with a pharmaceutically acceptable acid to afford a pharmaceutically acceptable salt of the compound of Formula II.

4. The process of claim 3, wherein deprotection of the compound of Formula IX is done in the presence of platinum oxide.

5. The process of claim 3, wherein said pharmaceutically acceptable acid is selected from hydrochloric acid and phosphoric acid.

\* \* \* \* \*